(12) United States Patent
Phares et al.

(10) Patent No.: US 10,167,247 B2
(45) Date of Patent: *Jan. 1, 2019

(54) SOLID FORMS OF TREPROSTINIL

(71) Applicant: United Therapeutics Corporation, Silver Spring, MD (US)

(72) Inventors: Kenneth Phares, Hillsborough, NC (US); Michael Scannell, Holly Springs, NC (US)

(73) Assignee: United Therapeutics Corporation, Silver Spring, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/793,009

(22) Filed: Oct. 25, 2017

(65) Prior Publication Data

US 2018/0072649 A1    Mar. 15, 2018

Related U.S. Application Data

(63) Continuation of application No. 14/200,575, filed on Mar. 7, 2014, now Pat. No. 9,822,057.

(60) Provisional application No. 61/781,303, filed on Mar. 14, 2013.

(51) Int. Cl.
  *C07C 59/72* (2006.01)
  *A61K 31/192* (2006.01)
  *C07C 51/41* (2006.01)

(52) U.S. Cl.
  CPC ............ *C07C 59/72* (2013.01); *A61K 31/192* (2013.01); *C07C 51/412* (2013.01)

(58) Field of Classification Search
  CPC ........ C07C 59/72; C07C 51/41; A61K 31/192
  See application file for complete search history.

(56) References Cited

U.S. PATENT DOCUMENTS

| | | | |
|---|---|---|---|
| 4,306,075 A | 12/1981 | Aristoff | |
| 4,306,076 A | 12/1981 | Nelson | |
| 4,338,457 A | 7/1982 | Aristoff | |
| 4,490,537 A | 12/1984 | Johnson | |
| 4,499,085 A | 2/1985 | Masuda | |
| 5,049,582 A | 9/1991 | Adler et al. | |
| 5,153,222 A | 10/1992 | Tadepalli et al. | |
| 5,234,953 A | 8/1993 | Crow et al. | |
| 5,466,713 A | 11/1995 | Blitstein-Willinger et al. | |
| 5,663,203 A | 9/1997 | Ekerdt et al. | |
| 5,814,301 A | 9/1998 | Klopp et al. | |
| 6,054,486 A | 4/2000 | Crow et al. | |
| 6,171,786 B1 | 1/2001 | Shtil et al. | |
| 6,441,245 B1 | 8/2002 | Moriarty et al. | |
| 6,451,815 B1 | 9/2002 | Hwang et al. | |
| 6,469,022 B1 | 10/2002 | Schellens | |
| 6,521,212 B1 | 2/2003 | Cloutier et al. | |
| 6,528,688 B2 | 3/2003 | Moriarty et al. | |
| 6,700,025 B2 | 3/2004 | Moriarty et al. | |
| 6,756,033 B2 | 6/2004 | Cloutier et al. | |
| 6,765,117 B2 | 7/2004 | Moriarty et al. | |
| 6,803,386 B2 | 10/2004 | Shorr et al. | |
| 6,809,223 B2 | 10/2004 | Moriarty et al. | |
| 7,199,157 B2 | 4/2007 | Wade et al. | |
| 7,384,978 B2 | 6/2008 | Phares et al. | |
| 7,417,070 B2 | 8/2008 | Phares et al. | |
| 7,544,713 B2 | 6/2009 | Phares et al. | |
| 7,879,909 B2 | 2/2011 | Wade et al. | |
| 7,999,007 B2 | 8/2011 | Jeffs et al. | |
| 8,232,316 B2 | 7/2012 | Phares et al. | |
| 8,242,305 B2 | 8/2012 | Batra et al. | |
| 8,252,839 B2 | 8/2012 | Phares et al. | |
| 8,349,892 B2 | 1/2013 | Phares | |
| 8,350,079 B2 | 1/2013 | Walsh | |
| 8,410,169 B2 | 4/2013 | Phares et al. | |
| 8,461,393 B2 | 6/2013 | Sharma | |
| 8,481,782 B2 | 7/2013 | Batra et al. | |
| 8,497,393 B2 | 7/2013 | Batra et al. | |
| 8,536,363 B2 | 9/2013 | Phares et al. | |
| 8,563,614 B2 | 10/2013 | Wade et al. | |
| 8,609,728 B2 | 12/2013 | Rothblatt et al. | |
| 8,653,137 B2 | 2/2014 | Jeffs et al. | |
| 8,658,694 B2 | 2/2014 | Jeffs et al. | |
| 9,822,057 B2 * | 11/2017 | Phares | C07C 59/72 |
| 2005/0085540 A1 | 4/2005 | Phares et al. | |
| 2005/0101608 A1 | 5/2005 | Santel | |
| 2005/0165111 A1 | 7/2005 | Wade et al. | |
| 2005/0254032 A1 | 11/2005 | Ozaki et al. | |
| 2005/0282901 A1 | 12/2005 | Phares et al. | |
| 2005/0282903 A1 | 12/2005 | Wade et al. | |
| 2007/0078095 A1 | 4/2007 | Phares et al. | |
| 2007/0078182 A1 | 4/2007 | Phares et al. | |

(Continued)

FOREIGN PATENT DOCUMENTS

| | | |
|---|---|---|
| CA | 2526534 A1 | 1/2005 |
| EP | 0 159 784 B1 | 10/1985 |

(Continued)

OTHER PUBLICATIONS

Badesch et al., "Prostanoid Therapy for Pulmonary Arterial Hypertension," Journal of the American College of Cardiology, 2004, 43(12:SupplS):56S-61S.

Bayés et al., "Gateways to Clinical Trials," Methods Find Exp. Clin. Pharmacol., Sep. 2003, 25(7):565-597.

Belch et al., "Randomnized, Double-Blind, Placebo-Controlled Study Evaluating the Efficacy and Safety of AS-013, a Prostaglandin $E_1$ Prodrug, in Patient With Intermittent Claudication," Circulation, The American Heart Association, Inc., vol. 95, No. 9, May 1997, pp. 2298-2301.

Berge et al., "Pharmaceutical Salts," Journal of Pharmaceutical Sciences, Jan. 1977, 66(1):1-20.

(Continued)

*Primary Examiner* — Yong S. Chong

(74) *Attorney, Agent, or Firm* — Foley & Lardner LLP

(57) ABSTRACT

There is provided individual polymorphic forms of treprostinil and pharmaceutical formulations comprising the same, methods of making and using the same.

42 Claims, 32 Drawing Sheets

(56) References Cited

U.S. PATENT DOCUMENTS

| | | | |
|---|---|---|---|
| 2007/0082948 | A1 | 4/2007 | Phares et al. |
| 2008/0200449 | A1 | 8/2008 | Olschweski et al. |
| 2008/0249167 | A1 | 10/2008 | Phares et al. |
| 2008/0280986 | A1 | 11/2008 | Wade et al. |
| 2009/0036465 | A1 | 2/2009 | Roscigno et al. |
| 2009/0124697 | A1 | 5/2009 | Cloutier et al. |
| 2010/0076083 | A1 | 3/2010 | Olschewski et al. |
| 2012/0190888 | A1 | 7/2012 | Batra et al. |
| 2012/0197041 | A1 | 8/2012 | Batra et al. |
| 2012/0216801 | A1 | 8/2012 | Olschewski et al. |
| 2012/0295980 | A1 | 11/2012 | Phares et al. |
| 2013/0261187 | A1 | 10/2013 | Phares et al. |
| 2014/0275616 | A1 | 9/2014 | Batra et al. |
| 2015/0005384 | A1 | 1/2015 | Tang et al. |
| 2015/0011637 | A1 | 1/2015 | Tang et al. |

FOREIGN PATENT DOCUMENTS

| | | |
|---|---|---|
| GB | 2 070 596 A | 9/1981 |
| WO | WO 99/021830 A1 | 5/1999 |
| WO | WO 99/25357 A1 | 5/1999 |
| WO | WO 00/57701 A1 | 10/2000 |
| WO | WO 2002/053517 A2 | 7/2002 |
| WO | WO 03/049676 A2 | 6/2003 |
| WO | WO 2005/007081 A1 | 1/2005 |
| WO | WO 2005/058303 A1 | 6/2005 |
| WO | WO 2012/009816 A1 | 1/2012 |
| WO | WO 2012/088607 A1 | 7/2012 |
| WO | WO 2013/016174 A1 | 1/2013 |
| WO | WO 2013/104317 A1 | 7/2013 |
| WO | WO 2013/104318 A1 | 7/2013 |

OTHER PUBLICATIONS

Bighley et al., "Salt Forms of Drugs and Absorption," Encyclopedia of Pharmaceutical Technology, Swarbrick et al., Eds., 1995, 13:453-499.

Braun-Moscovici et al., "Endothelin and Pulmonary Arterial Hypertension," Seminars in Arthritis and Rheumatism, Aug. 2004, 34(1):442-453.

Cahn, R.S. et al., "Specification of Molecular Chirality," Angew. Chem. Intern. Ed. Eng., 1966, 5(4):385-415.

Eells et al., "Advances in Prostacyclin Therapy for Pulmonary Arterial Hypertension," Critical Care Nurse, Apr. 2004, 24(2):42-48, 50-54.

Farrugia, L.J., "ORTEP-3 for Windows—a version of ORTEP-III with a Graphical User Interface (GUI)," J. Appl. Cryst., 1997, 30, 565.

Galiè et al., "Emerging Medical Therapies for Pulmonary Arterial Hypertension," Progress in Cardiovascular Diseases, Nov./Dec. 2002, 45(3):213-224.

Galiè et al., "Medical Therapy of Pulmonary Hypertension," Clinics in Chest Medicine, Sep. 2001, 22(3):529-537.

Galiè et al., "Prostanoids for Pulmonary Arterial Hypertension," Am. J. Respir. Med., 2003, 2(2):123-137.

Galiè et al., "The new clinical trials on pharmacological treatment in pulmonary arterial hypertension" Eur. Respir. J., 2002, 20:1037-1049.

Glusker et al., Crystal Structure Analysis: A Primer, $2^{nd}$ ed. Oxford University press: New York, 1985 p. 87.

Gould et al., "Salt selection for basic drugs," International Journal of Pharmaceutics, 1986, 33:201-217.

Hassner et al., "Direct Room Temperature Esterification of Carboxylic Acids" Tetrahedron Letters, Perganon Press Ltd., vol. 46, 1978, pp. 4475-4478.

Hoeper, M.M., "Pulmonary hypertension in collagen vascular disease," Eur. Respir. J., 2002, 19:571-576.

Huffman et al., "Pulmonary Arterial Hypertension: New Management Options," Curr. Treat. Options Cardiovasc. Med., Dec. 2004, 6(6):451-458.

Hussar, Daniel A., "New Drugs 2003, Part II," Nursing, Jul. 2003, 33(7):57-64.

Lee et al., "Efficient In Situ Esterification of Carboxylic Acids Using Cesium Carbonate," Organic Preparations and Procedures International, vol. 28, No. 4, Aug. 1996, pp. 480-483.

Lehman-McKeeman et al., "Diethanolamine Induces Hepatic Choline Deficiency in Mice," Toxicological Sciences, 2002, 67:38-45.

Macrae et al., "Mercury: visualization and analysis of crystal structures," J. Appl. Cryst., 2006, 39:453-457.

Maloney, James P., M.D., "Advances in the treatment of secondary pulmonary hypertension," Curr. Opin. Pulm. Med., Mar. 2003, 9(2):139-143.

Mann et al., Organic Syntheses, John Wiley & Sons, Inc., vol. 75, 1998, pp. 139-145.

McLaughlin et al., "Pulmonary Hypertension," Curr. Probl. Cardiol., Oct. 2004, 29(10):575-634.

Mohler, "Medical Management of Claudication," Up to Date, Inc., Mar. 31, 1997, pp. 1-6.

Mohler, "Clinical Manifestations of Claudication," Up to Date, Inc., Sep. 30, 1996, pp. 1-4.

Moriarty et al., "The Intramolecular Asymmetric Pauson-Khand Cyclization as a Novel and General Stereoselective Route to Benzindene Prostacyclins: Synthesis of UT-15 (Treprostinil)," J. Org. Chem. 2004, 69, 1890-1902.

Nagaya, Noritoshi, "Drug Therapy of Primary Pulmonary Hypertension," Am. J. Cardiovasc. Drugs, 2004, 4(2):75-85.

Neschis et al., "Surgical Indications for the Patient with Limb Threatening Ischemia," pp. 1-10.

Nielsen et al., "Evaluation of Glycolamide Esters and Various Other Esters of Aspirin as True Aspirin Prodrugs," J. Med. Chem., 1989, 32:727-734.

Okuda et al., "Acute Effect of Beraprost Sodium on Lower Limb Circulation in Patients with Non-Insulin-Dependent Diabetes Mellitus—Evaluation by Color Doppler Ultrasonography and Laser Cutaneous Blood Flowmetry," Prostaglandins, Elsevier, vol. 52, Nov. 1996, pp. 375-384.

Paramothayan et al., "Prostacyclin for pulmonary hypertension in adults (Review)," Cochrane Database Syst. Rev., 2003, 2:CD002994, 1-80.

Pass et al., "Current and Emerging Therapy for Primary Pulmonary Hypertension," The Annals of Pharmacotherapy, Sep. 2002, 36:1414-1423.

Patterson et al., "Acute Hemodynamic Effects of the Prostacyclin Analog 15AU81 in Service Congestive Heart Failure," The American Journal of Cardiology, vol. 75, Jan. 19, 1995, pp. 26A-33A.

Phares et al., "Stability and preservative effectiveness of treprostinil sodium after dilution in common intravenous diluents," Am. J. Health Syst. Pharm., May 1, 2003, 60:916-922.

Prelog et al., "Basic Principles of the CIP—System and Proposals for a Revision," Angew. Chem. Intern. Ed. Eng., 1982, 21, 567-583.

REMODULIN® Product Information brochure, United Therapeutics Corporation, approved by FDA for marketing on May 21, 2002, 13 pages.

Schermuly et al., "Subthreshold Doses of Specific Phosphodiesterase Type 3 and 4 Inhibitors Enhance the Pulmonary Vasodilatory Response to Nebulized Prostacyclin with Improvement in Gas Exchange," The Journal of Pharmacology and Experimental Therapeutics, 2000, 292(2):512-520.

Sheldrick, G. M., "A short history of SHELX," Acta Cryst., 2008, A64, 112-122.

Sorbera et al. "UT-15. Treatment of Pulmonary Hypertension Treatment of Peripheral Vascular Disease," *Drug of the Future*, 2001, 26(4), 364-374.

Spek, A. L., "Single-crystal structure validation with the program PLATON," J. Appl. Cryst., 2003, 36, 7-13.

Stahl et al., Eds., Handbook of Pharmaceutical Salts, 2002, 214-216, 314, 315 and 322.

Suleman et al., "Transition from Epoprostenol and Treprostinil to the Oral Endothelin Receptor Antagonist Bosentan in Patients with Pulmonary Hypertension," Chest, Sep. 2004, 126(3):808-815.

Sulica et al,. "Current Medical Treatment of Pulmonary Arterial Hypertension," Mount Sinai Journal of medicine, Mar. 2004, 71(2):103-114.

(56) References Cited

OTHER PUBLICATIONS

U.S. Food and Drug Administration Website entry regarding Diethanolamine, Dec. 21, 1999, updated Oct. 27, 2006, 1 page.
Vippagunta et al., "Crystalline solids," Advanced Drug Delivery Reviews, 2001, 48:3-26.
Wade et al., "Effect of Continuous Subcutaneous Treprostinil Therapy on the Pharmacodynamics and Pharmacokinetics of Warfarin," J. Cardiovasc. Pharmacal., Jun. 2003, 41(6):908-915.
Zamudio, Tomas Pulido, "Que es lo nuevo en el tratamiento de la hipertension arterial pulmonar?" Archivos de Cardiologia de Mexico, Apr.-Jun. 2003, 73(Suppl):S121-S124.
How is Pulmonary Hypertension treated? NHLBI, NIH, http://www.nhlbi.nih.gov/health/health-topics/topics/pah/treatment, Aug. 2, 2011.
Noriaki, Hirayama, "Handbook of production of organic compound crystals, Principle and know-how," Maruzen Co., Ltd., Jul. 25, 2008, 57-84, with partial English translation of indicated portion.

\* cited by examiner (top to bottom)
Form A
Form B
Material C

SOLID FORMS OF TREPROSTINIL

RELATED APPLICATIONS

The present application is a Continuation of U.S. application Ser. No. 14/200,575, filed Mar. 7, 2014, which claims priority to U.S. provisional patent application No. 61/781,303 filed Mar. 14, 2013, which are incorporated herein by reference in their entirety.

FIELD

The present application relates in general to solid forms of prostacyclin derivatives and in particular, to solid forms of treprostinil and methods of making and using thereof.

SUMMARY

One embodiment is crystalline treprostinil monohydrate Form A, characterized by an X-ray powder diffractogram comprising the following peaks: 11.6, 16.2, and 20.0°2θ±0.2°2θ, as determined on a diffractometer using Cu-Kα radiation at a wavelength of 1.54184 Å having a purity of at least 90% aside from residual solvents. In another embodiment, the diffractogram further comprises peaks at 5.2, 21.7 and 27.7°2θ±0.2°2θ. In yet another embodiment, the diffractogram is substantially as shown in FIG. 2.

An additional embodiment is crystalline treprostinil monohydrate Form B, characterized by an X-ray powder diffractogram comprising the following peaks: 5.9, 12.1, and 24.4°2θ±0.2°2θ, as determined on a diffractometer using Cu-Kα radiation at a wavelength of 1.54184 Å having a purity of at least 90% aside from residual solvents. In another embodiment, the diffractogram further comprises peaks at 10.7, 20.6 and 22.3°2θ±0.2°2θ. In yet another embodiment, the diffractogram is substantially as shown in FIG. 9.

Yet another embodiment is method of making the crystalline treprostinil monohydrate Form A comprising agitating anhydrous or wet treprostinil in an aprotic organic solvent and water followed by removal of the solvent by air-drying the solid at a temperature from about 15° C. to about 35° C. until no additional solvent evaporates.

Still another embodiment is a method of making the crystalline treprostinil monohydrate Form B comprising agitating anhydrous or wet treprostinil in a protic organic solvent and water followed by removal of the solvent by air-drying the solid at a temperature from about 15° C. to about 35° C. until no additional solvent evaporates.

One embodiment is a composition comprising substantially one form of treprostinil monohydrate Form A or treprostinil monohydrate Form B.

In another embodiment, there is a method of treating a medical condition, comprising administering to a subject in need thereof a pharmaceutical formulation that comprises a therapeutically effective amount of treprostinil monohydrate Form A or treprostinil monohydrate Form B.

In one embodiment, there is further provided a method of using treprostinil monohydrate form A or B in treating medical conditions, including those for which it is known in the art to use treprostinil, such as those described in *Drug of the Future*, 2001, 26(4), 364-374, U.S. Pat. Nos. 5,153,222; 5,234,953; 6,521,212; 6,756,033; 6,803,386; 7,199,157; 6,054,486; 7,417,070; 7,384,978; 7,879,909; 8,563,614; 8,252,839; 8,536,363; 8,410,169; 8,232,316; 8,609,728; 8,350,079; 8,349,892; 7,999,007; 8,658,694; 8,653137; US patent application publications nos. 2005/0165111; 2009/0036465; 2008/0200449; 2010-0076083; 2012-0216801; 2008/0280986; 2009-0124697; 2013-0261187

DETAILED DESCRIPTION

Figure 1:
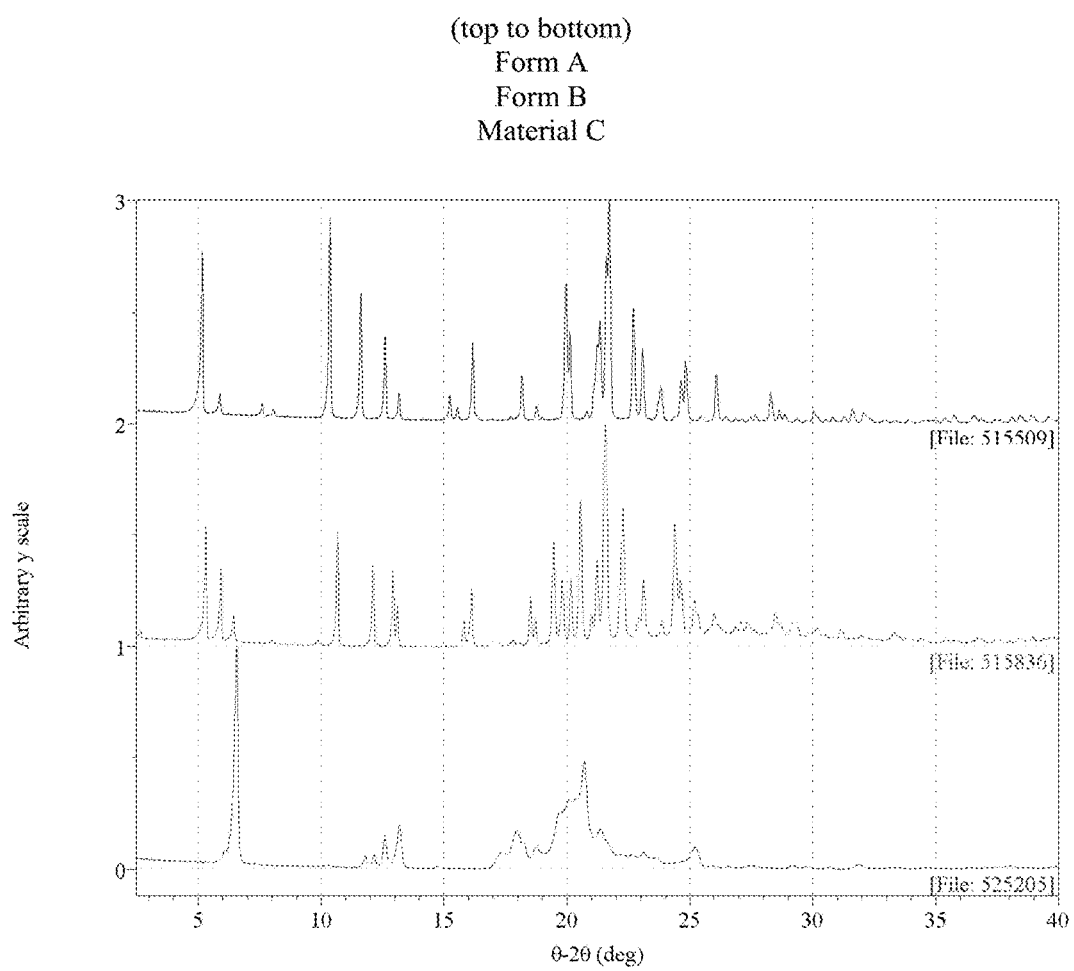
FIG. 1 is a comparison between the XRPD patterns of the unique crystalline XRPD patterns from solid form screen of treprostinil.

Unless otherwise specified, "a" or "an" means "one or more".

Prostacyclin derivatives are useful pharmaceutical compounds possessing activities such as platelet aggregation inhibition, gastric secretion reduction, lesion inhibition, and bronchodilation.

Treprostinil, the active ingredient in Remodulin®, Tyvaso® and Orenitram™, was first described in U.S. Pat. No. 4,306,075. Methods of making treprostinil and other prostacyclin derivatives are described, for example, in Moriarty, et al in J. Org. Chem. 2004, 69, 1890-1902, Drug of the Future, 2001, 26(4), 364-374, U.S. Pat. Nos. 6,441,245; 6,528,688; 6,700,025; 6,809,223; 6,756,117; 8,461,393; 8,481,782; 8,242,305; 8,497,393; US patent applications nos. 2012-0190888 and 2012-0197041; PCT publication no. WO2012/009816.

Various uses and/or various forms of treprostinil are disclosed, for examples, in U.S. Pat. Nos. 5,153,222; 5,234,953; 6,521,212; 6,756,033; 6,803,386; 7,199,157; 6,054,486; 7,417,070; 7,384,978; 7,879,909; 8,563,614; 8,252,839; 8,536,363; 8,410,169; 8,232,316; 8,609,728; 8,350,079; 8,349,892; 7,999,007; 8,658,694; 8,653137; US patent application publications nos. 2005/0165111; 2009/0036465; 2008/0200449; 2010-0076083; 2012-0216801; 2008/0280986; 2009-0124697; 2013-0261187; PCT publication no. WO00/57701; U.S. provisional application No. 61/791,015 filed Mar. 15, 2013. The teachings of the aforementioned references are incorporated by reference to show how to practice the embodiments of the present invention.

In sum, treprostinil is of great importance from a medicinal point of view. Therefore, a need exists for a stable form of treprostinil, which presents advantage in storage, shipment, handling, and formulation, for example.

The present invention relates to novel forms of treprostinil, including novel forms of treprostinil monohydrate and anhydrous treprostinil.

Treprostinil is the active ingredient of Remodulin®, which has been approved by the U.S. FDA for the treatment of Pulmonary Arterial Hypertension (PAH) in patients with NYHA Class II, III and IV symptoms to diminish symptoms associated with exercise using subcutaneous or intravenous administration. Treprostinil is also the active ingredient in Tyvaso® inhalation solution and Orenitram™ extended-release tablets.

Treprostinil's chemical name is 2-((1R,2R,3aS,9aS)-2-hydroxy-1-((S)-3-hydroxyoctyl)-2,3,3a,4,9,9a-hexahydro-1H-cyclopenta[b]naphthalen-5-yloxy)acetic acid of the following structure:

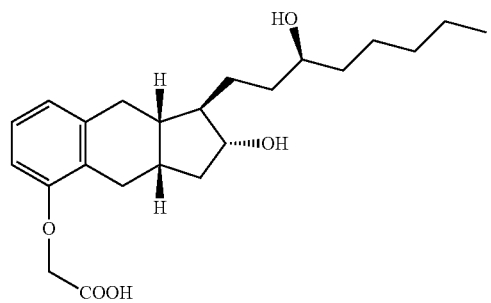 [SMILES: CCCCC[C@H](O)CC[C@@H]1[C@H]2Cc3cccc(OCC(=O)O)c3C[C@H]2C[C@H]1O]

An anhydrous form of treprostinil has been previously described, e.g., in J. Org. Chem. 2004, 69, 1890-1902. The anhydrous form is not stable at room temperature. Stability tests show that anhydrous treprostinil is not stable at 25° C. and dimers formed upon standing. A larger amount of dimers can form at higher temperatures. However, dimer formation is negligible at 5° C. Therefore, anhydrous treprostinil must be refrigerated for storage and transport. In the past, anhydrous treprostinil had to be refrigerated and shipped with ice packs to maintain low (2° C.-8° C.) temperatures.

The monohydrate of treprostinil has been previously described, e.g. in U.S. Pat. No. 8,350,079, the contents of which are incorporated by reference in their entirety. The monohydrate of treprostinil was previously described; however, the polymorphic forms of treprostinil monohydrate and anhydrous treprostinil disclosed herein were not described.

Solid Forms of Treprostinil

As described generally above, the present disclosure provides solid crystalline forms of treprostinil in Forms A, B and Form C. Form A was surprisingly found to be more easily filterable and easier to isolate than the prior art compounds. The Form C may form upon drying Form A or Form B under reduced pressure and a temperature of less than 42° C.

Crystalline treprostinil monohydrate Form A is characterized by its X-ray powder diffractogram that comprises peaks at 11.6, 16.2, and 20.0°2θ±0.2°2θ, as determined on a diffractometer using Cu-Kα radiation at a wavelength of 1.54059 Å. The diffractogram comprises additional peaks at 5.2, 21.7 and 27.7°2θ±0.2°2θ. Form A may also be characterized by one or more peaks in Table 1. Form A also is characterized by its full X-ray powder diffractogram as substantially shown in FIG. 2.

Figure 3:
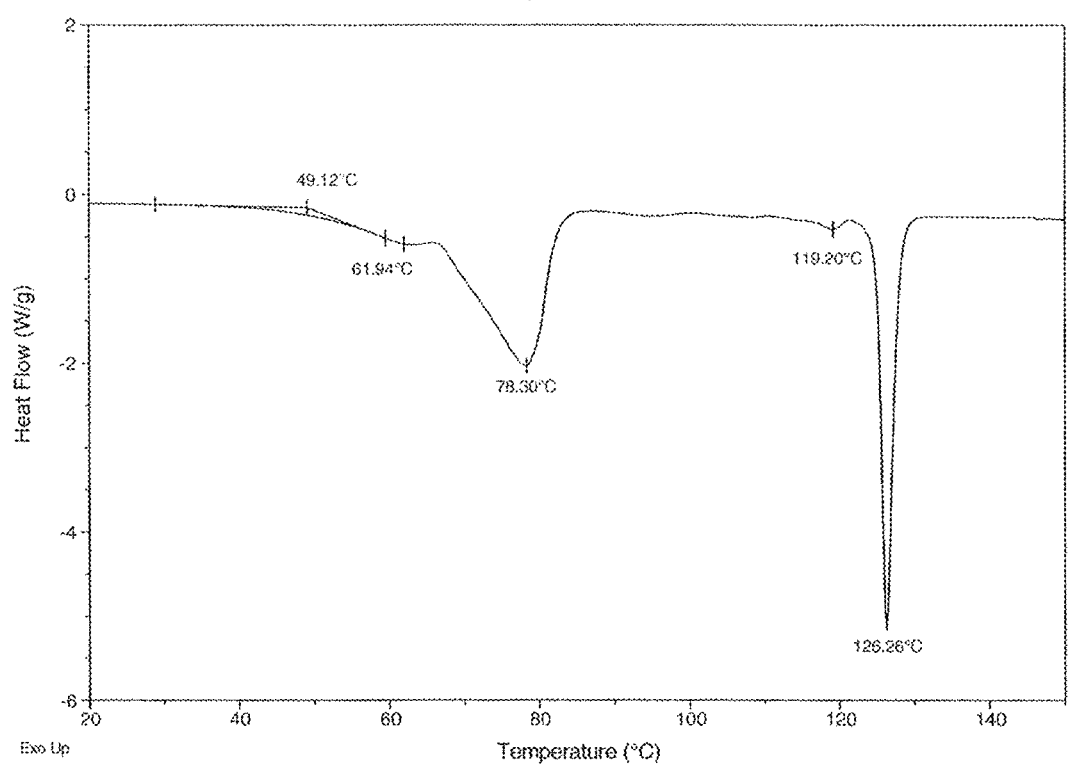
FIG. 3 is a differential scanning calorimetry thermogram of treprostinil monohydrate Form A.
Figure 4:
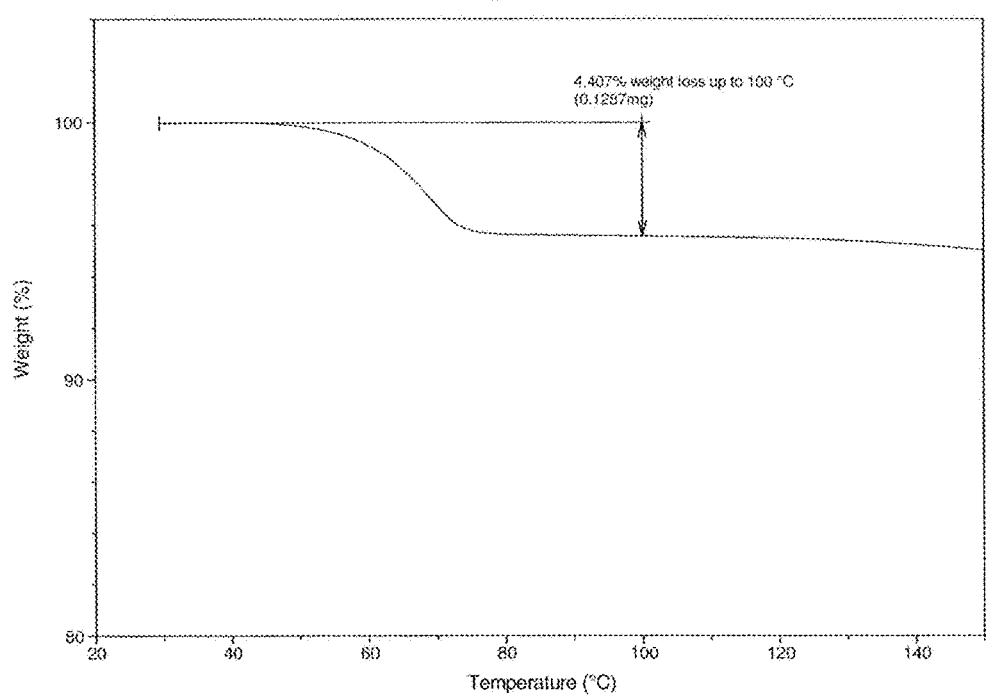
FIG. 4 is a thermogravimetric thermogram of treprostinil monohydrate Form A.
Figure 5:
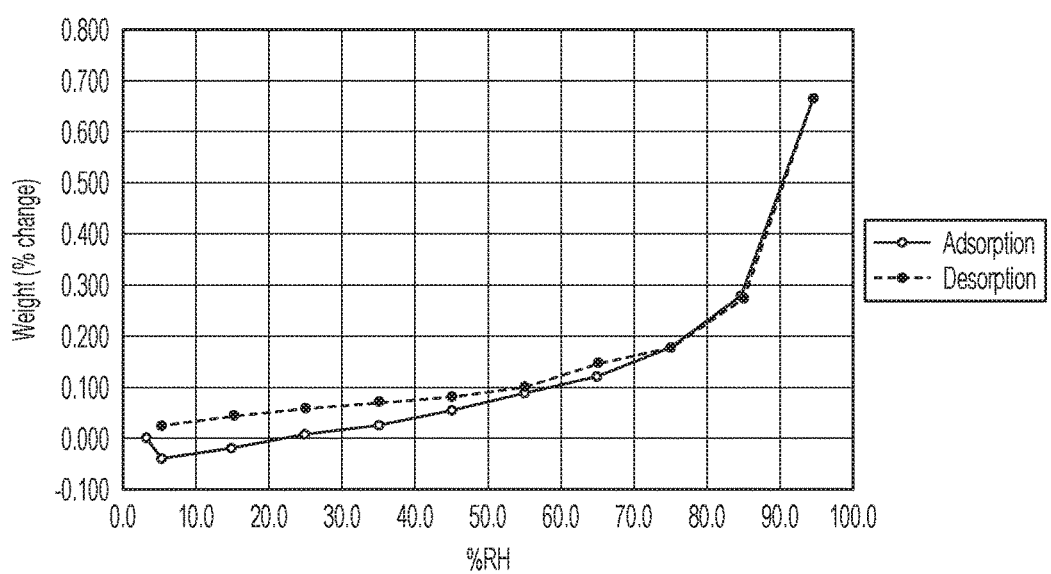
FIG. 5 is a dynamic vapor sorption/desorption isotherm of Treprostinil monohydrate Form A.
Figure 6:
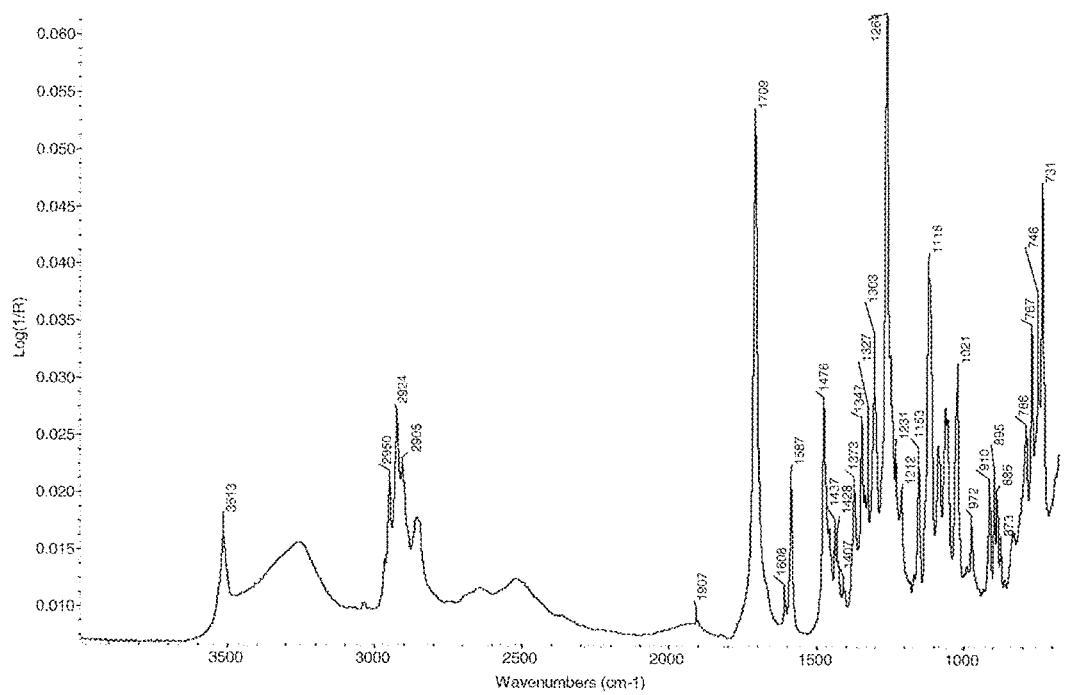
FIG. 6 is an infrared spectrum of treprostinil monohydrate Form A.
Figure 7:
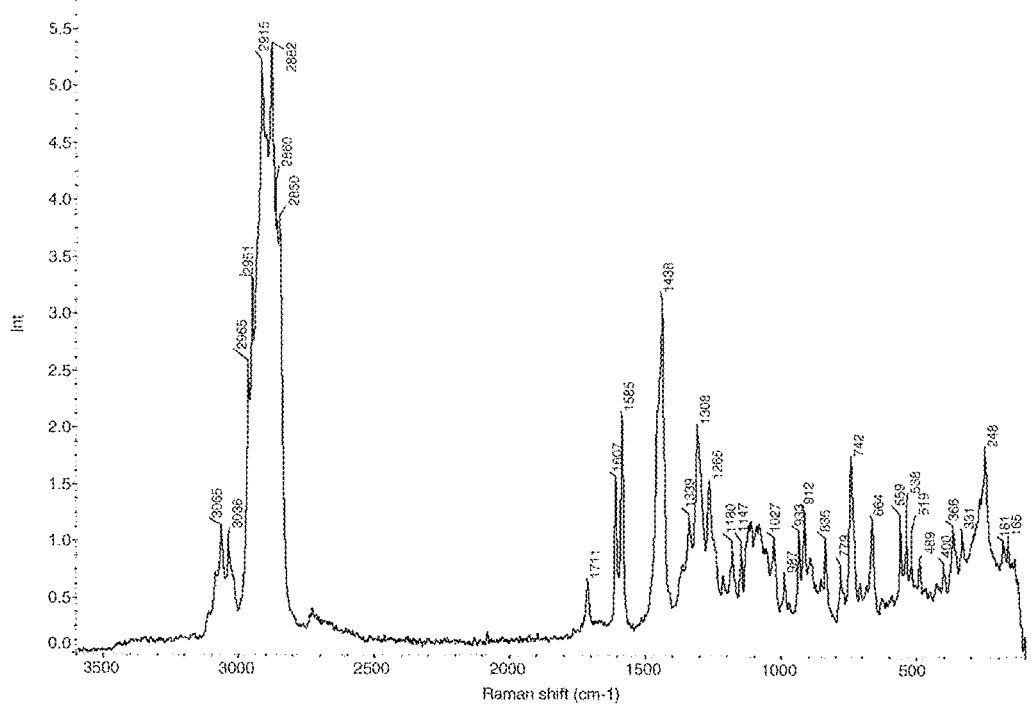
FIG. 7 is a raman spectrum of treprostinil monohydrate Form A.
Figure 8:
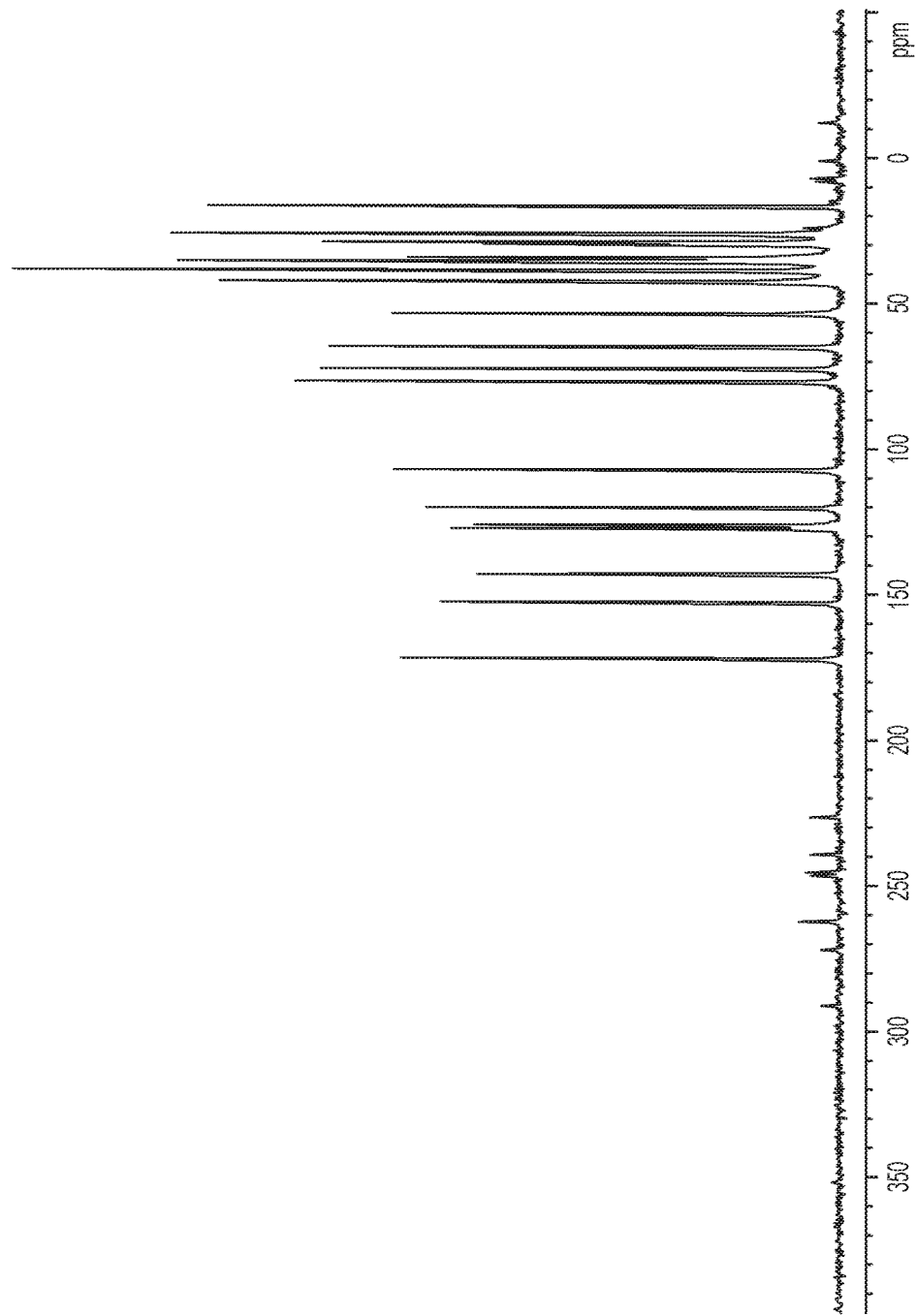
FIG. 8 is a solid state $^{13}$C cross polarization magic angle spinning nuclear magnetic resonance spectrum of treprostinil monohydrate Form A.

In some embodiments, Form A is characterized by its differential scanning calorimetry (DSC) curve that comprises a minor endotherm at about 78.3° C. and a major endotherm at about 126.3° C. Form A also is characterized by its full DSC curve as substantially as shown in FIG. 3.

In an embodiment, Form A is produced substantially free of any other form of crystalline treprostinil. In another embodiment, Form A has a purity of at least 90%, 95%, 98%, 99%, or 99.9% aside from residual solvents. Purity may be determined by a manner known in the art, such as NMR integration. It may also be determined by the lack, or reduction, of peaks corresponding to other forms of crystalline treprostinil in the XRPD. In one embodiment, the crystalline treprostinil monohydrate Form A is in substantially pure form. In one embodiment, Form A is obtained in one or more of the purities disclosed above in an amount of 1 gram to 50 kg. In one embodiment, the Form A is obtained in one or more of the purities disclosed above in an amount understood by one of skill in the art to be sufficient for industrial scale production of treprostinil.

Crystalline treprostinil monohydrate Form B is characterized by its X-ray powder diffractogram that comprises peaks at 5.9, 12.1, and 24.4°2θ±0.2°2θ, as determined on a diffractometer using Cu-Kα radiation at a wavelength of 1.54059 Å. The diffractogram comprises additional peaks at 10.7, 20.6 and 22.3°2θ±0.2°2θ. Form B may also be characterized by one or more peaks in Table 3. Form B also is characterized by its full X-ray powder diffractogram as substantially shown in FIG. 9.

Figure 10:
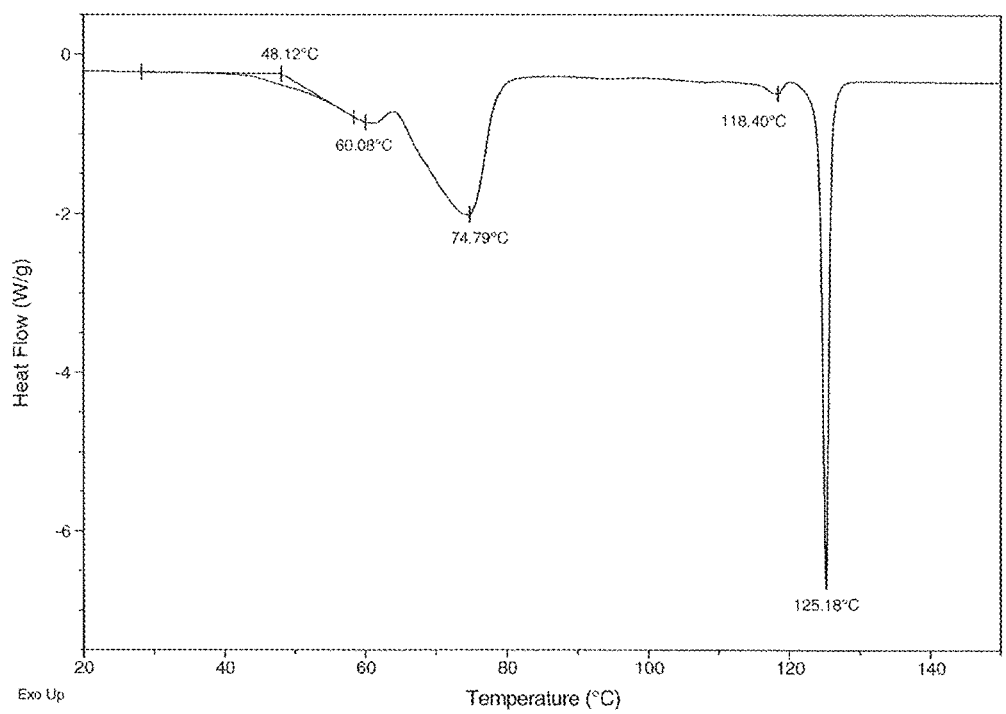
FIG. 10 is a differential scanning calorimetry thermogram of treprostinil monohydrate Form B.
Figure 11:
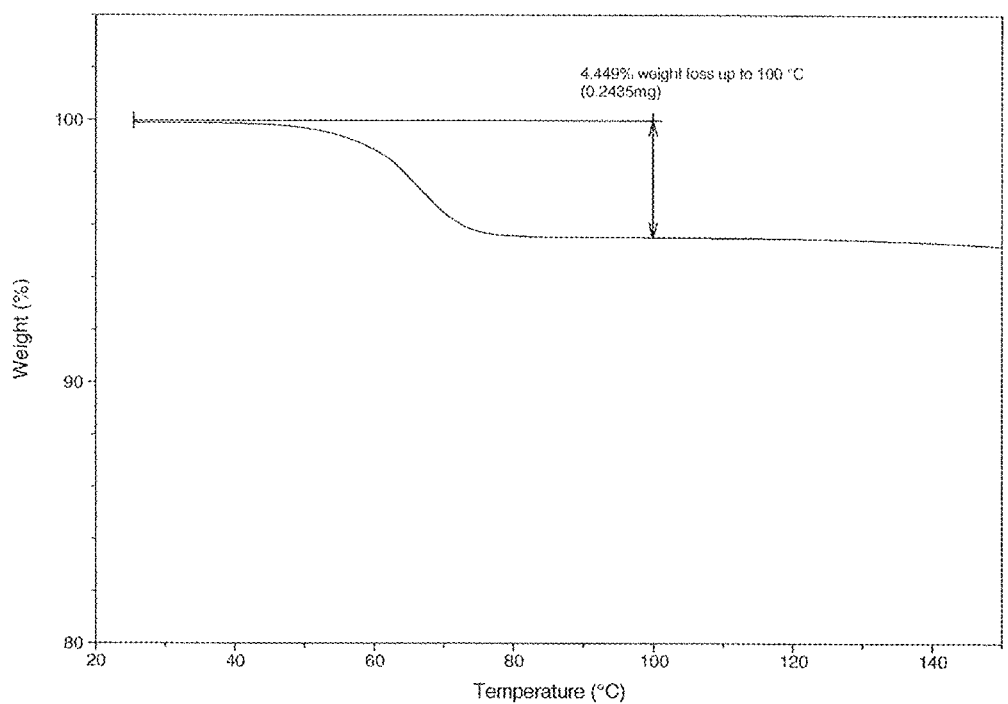
FIG. 11 is a thermogravimetric thermogram of treprostinil monohydrate Form B.
Figure 12:
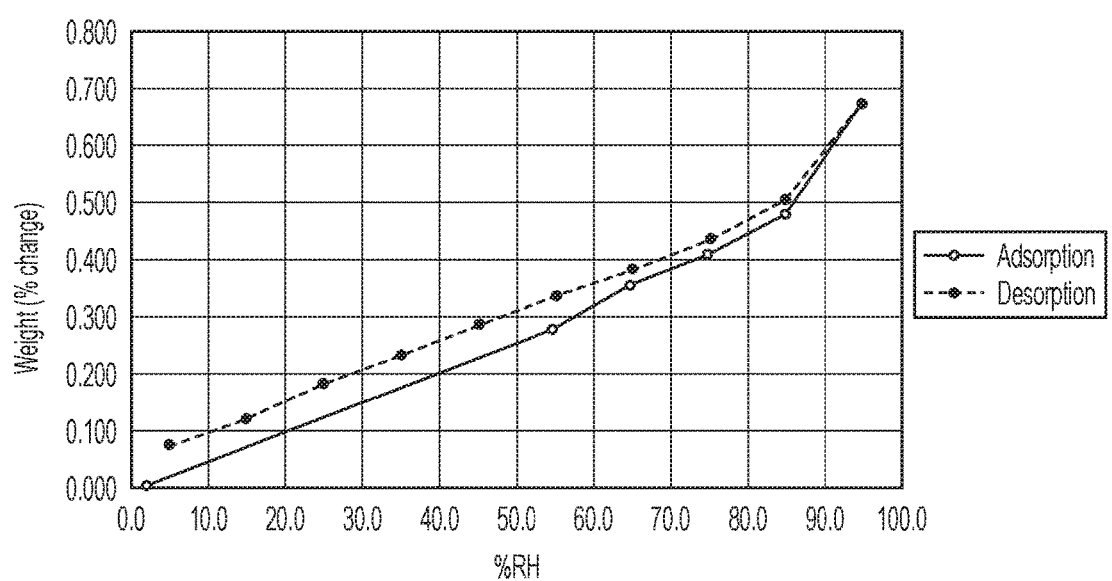
FIG. 12 is a dynamic vapor sorption/desorption isotherm of Treprostinil monohydrate Form B.
Figure 13:
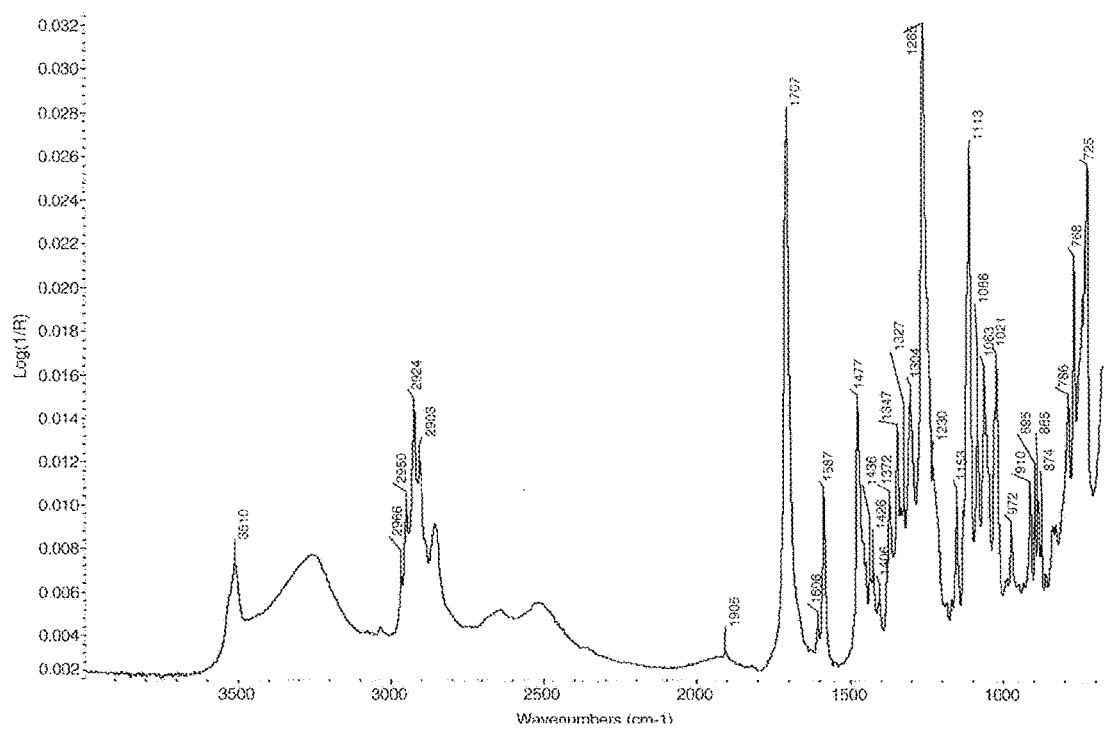
FIG. 13 is an infrared spectrum of treprostinil monohydrate Form B.
Figure 14:
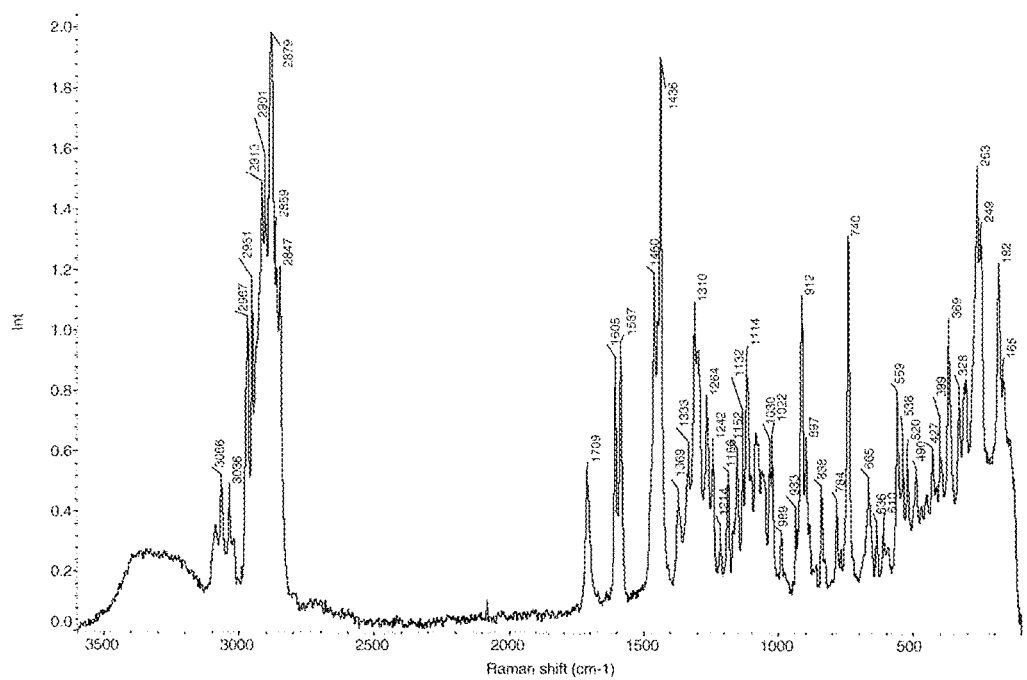
FIG. 14 is a raman spectrum of treprostinil monohydrate Form B.
Figure 15:
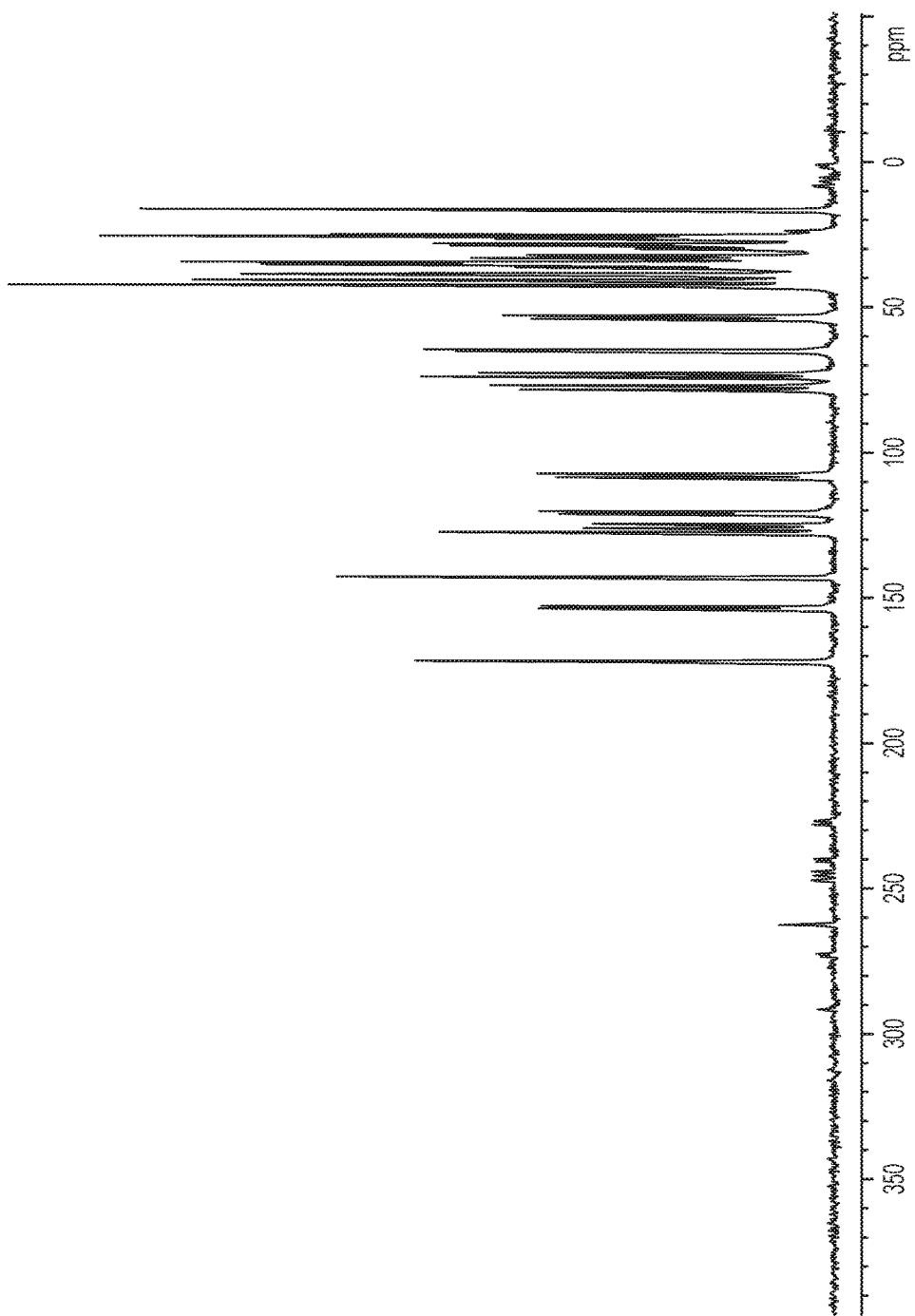
FIG. 15 is a solid state $^{13}$C cross polarization magic angle spinning nuclear magnetic resonance spectrum of treprostinil monohydrate Form B.

In some embodiments, Form B is characterized by its differential scanning calorimetry (DSC) curve that comprises a minor endotherm at about 78.3° C. and a major endotherm at about 126.3° C. Form B also is characterized by its full DSC curve as substantially as shown in FIG. 10.

In an embodiment, Form B is produced substantially free of any other form of crystalline treprostinil. In another embodiment, Form B has a purity of at least 90%, 95%, 98%, 99%, or 99.9% aside from residual solvents. Purity may be determined by a manner known in the art, such as NMR integration. It may also be determined by the lack, or reduction, of peaks corresponding to other forms of crystalline treprostinil in the XRPD. In one embodiment, the crystalline treprostinil monohydrate Form B is in substantially pure form. In one embodiment, Form B is obtained in one or more of the purities disclosed above in an amount of 1 gram to 50 kg. In one embodiment, the Form B is obtained in one or more of the purities disclosed above in an amount understood by one of skill in the art to be sufficient for industrial scale production of treprostinil.

Anhydrous treprostinil Form C is characterized by its X-ray powder diffractogram that comprises a peak at 6.55°2θ±0.2°2θ, as determined on a diffractometer using Cu-Kα radiation at a wavelength of 1.54059 Å. Form C may also be characterized by one or more peaks in Table 1. Form C also is characterized by its full X-ray powder diffractogram as substantially shown in FIG. 16.

Figure 17:
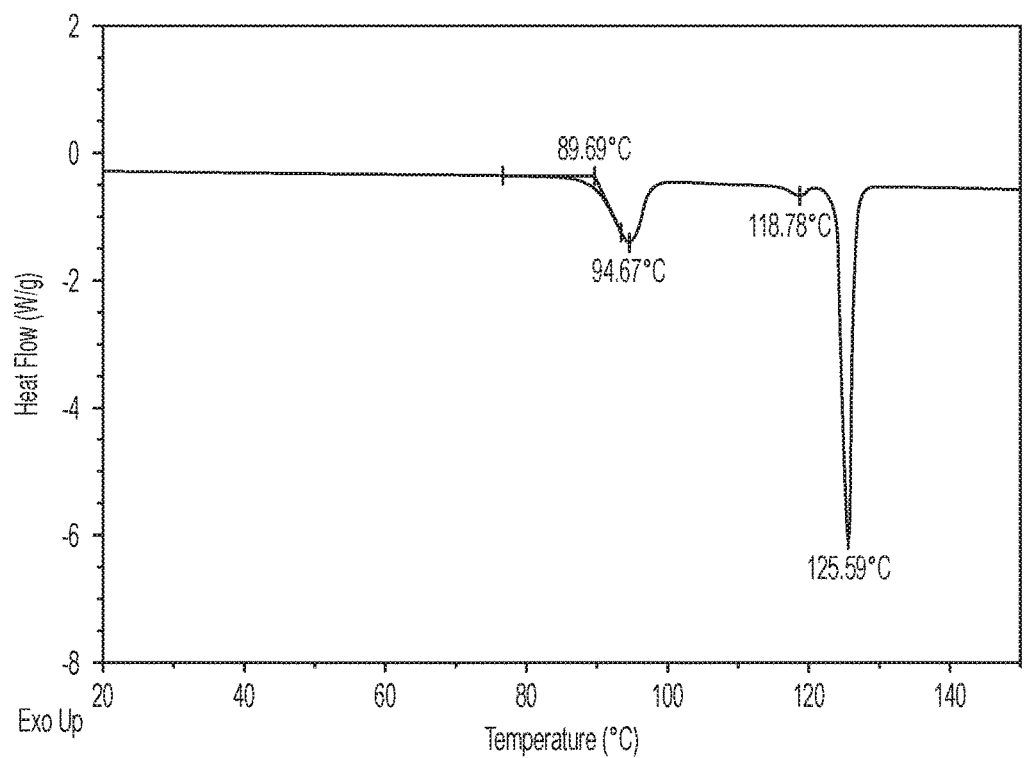
FIG. 17 is a differential scanning calorimetry thermogram of Treprostinil Form C.

In some embodiments, Form C is characterized by its differential scanning calorimetry (DSC) curve that comprises a minor endotherm at about 78.3° C. and a major endotherm at about 126.3° C. Form C also is characterized by its full DSC curve as substantially as shown in FIG. 17.

In an embodiment, Form C is produced substantially free of any other form of crystalline treprostinil. In another embodiment, Form C has a purity of at least 90%, 95%, 98%, 99%, or 99.9% aside from residual solvents. Purity may be determined by a manner known in the art, such as NMR integration. It may also be determined by the lack, or reduction, of peaks corresponding to other forms of crystalline treprostinil in the XRPD. In one embodiment, the anhydrous treprostinil Form C is in substantially pure form. Anhydrous treprostinil Form C differs from polymorphic treprostinil, as can be seen by the corresponding XRPD. In one embodiment, Form C is obtained in one or more of the purities disclosed above in an amount of 1 gram to 50 kg. In one embodiment, the Form C is obtained in one or more of the purities disclosed above in an amount understood by one of skill in the art to be sufficient for industrial scale production of treprostinil.

Mesophase treprostinil is characterized by its X-ray powder diffractogram that comprises a lack of substantial peaks between 5.0 and 40°2θ±0.2°2θ, as determined on a diffractometer using Cu-Kα radiation at a wavelength of 1.54059 Å. Mesophase treprostinil also is characterized by one or more peaks in its X-ray powder diffractogram as substantially shown in any one of the X-ray powder diffractogram of FIGS. 31-32. Mesophase treprostinil also is characterized by its partial X-ray powder diffractogram as substantially shown in any one of the X-ray powder diffractogram of FIGS. 31-32.

In an embodiment, Mesophase treprostinil is produced substantially free of any form of crystalline treprostinil. In another embodiment, Mesophase treprostinil has a purity of at least 90%, 95%, 98%, 99%, or 99.9% aside from residual solvents. Purity may be determined by a manner known in the art, such as NMR integration. It may also be determined by the lack, or reduction, of peaks corresponding to other forms of crystalline treprostinil in the XRPD. In one embodiment, the Mesophase treprostinil is in substantially pure form. Mesophase treprostinil differs from polymorphic treprostinil, as can be seen by the corresponding XRPD. In one embodiment, Mesophase treprostinil is obtained in one or more of the purities disclosed above in an amount of 1 gram to 50 kg. In one embodiment, the Mesophase treprostinil is obtained in one or more of the purities disclosed above in an amount understood by one of skill in the art to be sufficient for industrial scale production of treprostinil.

Figure 31:
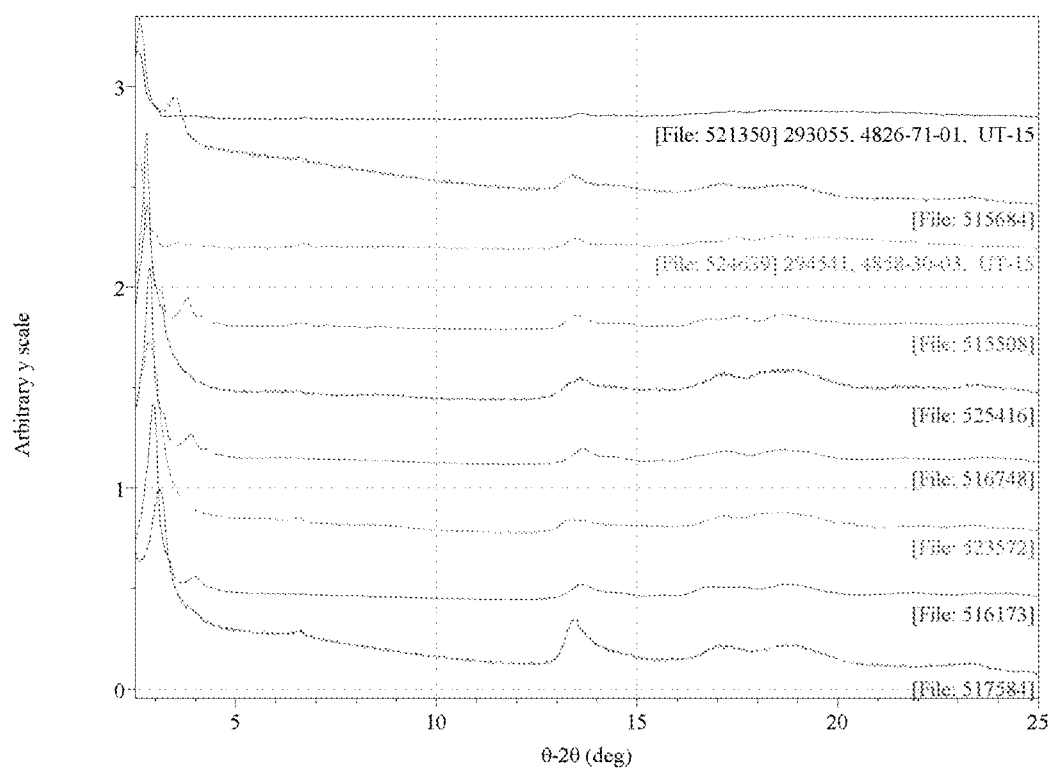
FIG. 31 is X-ray powder diffraction pattern of mesophase treprostinil.
Figure 32:
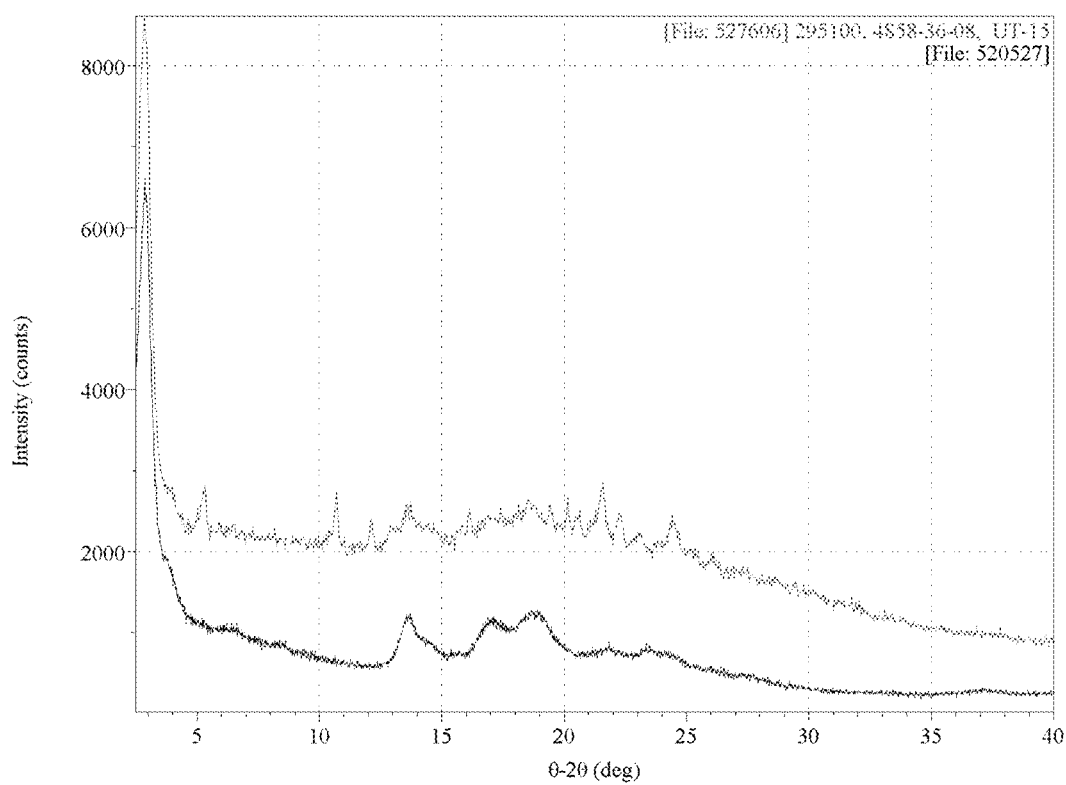
FIG. 32 is X-ray powder diffraction pattern of mesophase treprostinil.

The mesophase treprostinil of FIG. 31 are formed, from top to bottom, from the following solutions: (1) 0.40 water activity slurry with acetone 2 days; (2) DCM slurry 60 to 30° C.; (3) 0.80 water activity slurry with isopropanol 7 days; (4) 1-propanol/water 1:1 v/v slurry ambient temperature; (5) Form B+A+mesophase 50° C. 7 days, (6) Acetonitrile slurry ambient temperature; (7) Form A 50° C. 15 hours; (8) Methanol/ethyl acetate evaporation; (9) Toluene crash precipitation from methyl ethyl ketone. Mesophase treprostinil can also be formed by the following methods, as shown in FIG. 32 97% RH 12 days; mesophase+weak Form B (top) Before stress; mesophase (bottom).

Compositions and Uses of Solid Forms of Treprostinil

Another embodiment is a pharmaceutical formulation comprising treprostinil monohydrate Form A or Form B or anhydrous treprostinil Form C and a pharmaceutically acceptable carrier or excipient.

The term "pharmaceutical" when used herein as an adjective means substantially non-deleterious to the recipient mammal. By "pharmaceutical formulation" it is meant the carrier, diluent, excipients and active ingredient(s) must be compatible with the other ingredients of the formulation, and not deleterious to the recipient thereof.

Treprostinil monohydrate Form A or Form B, or Form C, can be formulated prior to administration. The selection of the formulation should be decided by the attending physician taking into consideration the same factors involved with determining the effective amount.

The total active ingredients in such formulations comprises from 0.1% to 99.9% by weight of the formulation. Treprostinil monohydrate Form A or Form B, or anhydrous treprostinil Form C, can be formulated with one or more additional active ingredients or as the sole active ingredient.

Pharmaceutical formulations of the present invention are prepared by procedures known in the art using well known and readily available ingredients. For example, treprostinil monohydrate Form A or Form B or Form C, either alone, or in combination with other active ingredient(s) are formulated with common excipients, diluents, or carriers, and formed into tablets, capsules, suspensions, solutions, injectables, aerosols, powders, and the like.

Pharmaceutical formulations of this invention for parenteral administration comprise sterile aqueous or non-aqueous solutions, dispersions, suspensions, or emulsions, as well as sterile powders which are reconstituted immediately prior to use into sterile solutions or suspensions. Examples of suitable sterile aqueous and non-aqueous carriers, diluents, solvents or vehicles include water, physiological saline solution, ethanol, polyols (such as glycerol, propylene glycol, poly(ethylene glycol), and the like), and suitable mixtures thereof, vegetable oils (such as olive oil), and injectable organic esters such as ethyl oleate. Proper fluidity is maintained, for example, by the use of coating materials such as lecithin, by the maintenance of proper particle size in the case of dispersions and suspensions, and by the use of surfactants.

Parenteral formulations may also contain adjuvants such as preservatives, wetting agents, emulsifying agents, and dispersing agents. Prevention of the action of microorganisms is ensured by the inclusion of antibacterial and antifungal agents, for example, paraben, chlorobutanol, phenol sorbic acid, and the like. It may also be desirable to include isotonic agents such as sugars, sodium chloride, and the like. Injectable formulations are sterilized, for example, by filtration through bacterial-retaining filters, or by presterilization of the components of the mixture prior to their admixture, either at the time of manufacture or just prior to administration (as in the example of a dual chamber syringe package).

Solid dosage forms for oral administration include capsules, tablets, pills, powders, and granules. In such solid dosage forms, treprostinil monohydrate Form A or Form B, or anhydrous treprostinil Form C, is mixed with at least one inert, pharmaceutical carrier such as sodium citrate, or dicalcium phosphate, and/or (a) fillers or extenders such as starches, sugars including lactose and glucose, mannitol, and silicic acid, (b) binding agents such as carboxymethylcellulose and other cellulose derivatives, alginates, gelatin, poly(vinylpyrrolidine), sucrose and acacia, (c) humectants such as glycerol, (d) disintegrating agents such as agar-agar, calcium carbonate, sodium bicarbonate, potato or tapioca starch, alginic acid, silicates and sodium carbonate, (e) moisturizing agents such as glycerol; (f) solution retarding agents such as paraffin, (g) absorption accelerating agents such as quaternary ammonium compounds, (h) wetting agents such as cetyl alcohol and glycerin monostearate, (i) absorbents such as kaolin and bentonite clay, and (j) lubricants such as talc, calcium stearate, magnesium stearate, solid poly(ethylene glycols), sodium lauryl sulfate, and mixtures thereof. In the case of capsules, tablets and pills, the dosage form may also contain buffering agents.

Solid formulations of a similar type may also comprise the fill in soft or hard gelatin capsules using excipients such as lactose as well as high molecular weight poly(ethylene glycols) and the like. Solid dosage forms such as tablets, dragees, capsules, pills and granules can also be prepared with coatings or shells such as enteric coatings or other coatings well known in the pharmaceutical formulating art. The coatings may contain opacifying agents or agents which release the active ingredient(s) in a particular part of the digestive tract, as for example, acid soluble coatings for release of the active ingredient(s) in the stomach, or base soluble coatings for release of the active ingredient(s) in the intestinal tract. The active ingredient(s) may also be microencapsulated in a sustained-release coating, with the microcapsules being made part of a pill of capsule formulation. Use of treprostinil monohydrate Form A or Form B, or anhydrous treprostinil Form C in solid dosage forms as tablets, dragees, capsules, pills and granules may be preferred.

Another embodiment is a method of treating a medical condition comprising administering a therapeutically effective amount of the aforementioned pharmaceutical formulation, such a solid formulation, comprising the treprostinil monohydrate Form A or Form B, or anhydrous treprostinil Form C, to a subject, such as a human, in need thereof. The medical conditions being treated include but not limited to pulmonary hypertension (including primary and secondary pulmonary hypertension and pulmonary arterial hypertension), congestive heart failure, peripheral vascular disease, asthma, severe intermittent claudication, immunosuppression, proliferative diseases, cancer such as lung, liver, brain, pancreatic, kidney, prostate, breast, colon and head-neck cancer, ischemic lesions, neuropathic foot ulcers, and pulmonary fibrosis, kidney function, and interstitial lung disease. In some embodiments, the pharmaceutical formulation may comprise one or more active ingredients in addition to treprostinil monohydrate Form A or Form B, or anhydrous treprostinil Form C.

Treprostinil monohydrate Form A or Form B, or anhydrous treprostinil Form C may be also used for storing, shipping and/or handling treprostinil.

Methods of Making

The Form A and Form B of treprostinil can be made by slurrying or precipitating from an aqueous organic solvent. For example, an organic solvent and greater than or equal to about 50 percent v/v water may be used. In one embodiment, the water content of the aqueous organic solvent is from about 50 percent to about 60 or 70 or 80 percent (v/v). One of skill will understand that the slurry may comprise the water during part or all of the agitation, while the water in the precipitation may be added or increased at a point to reduce the solubility of the treprostinil and cause precipitation.

One embodiment is a method of making the crystalline treprostinil monohydrate Form A comprising agitating anhydrous or wet treprostinil in an organic solvent and water followed by removal of the solvent by air-drying the solid at a temperature from about 15° C. to about 35° C. until no additional solvent evaporates. In one embodiment the organic solvent is an aprotic and/or non-polar organic solvent. Examples of non-polar and/or aprotic organic solvents include, but not limited to, hexane, benzene, toluene, 1,4-dioxane, chloroform, diethyl ether, dicholormetane, tetrahydrofuran, ethyl acetate, acetone, dimethylformamide, acetonitrile, dimethyl sulfoxide and their combinations. In one embodiment the organic solvent is acetone or 1,4-dioxane. In one embodiment, the agitation is in the form of a slurry in 1,4-dioxane/$H_2O$ or precipitated from acetone w/$H_2O$. In one embodiment, the organic solvent is not ethanol. In one embodiment the air-drying temperature is about 15° C. to about 25° C., or any temperature or range therein between.

One embodiment is a method of making the crystalline treprostinil monohydrate Form B comprising agitating anhydrous or wet treprostinil in an organic solvent and water followed by removal of the solvent by air-drying the solid at a temperature from about 15° C. to about 35° C. until no additional solvent evaporates. In one embodiment the organic solvent is a protic organic solvent. Examples of protic organic solvents include but not limited to formic acid, n-butanol, isopropanol, nitromehtane, methanol, acetic acid. In one embodiment the organic solvent is methanol. In one embodiment, the agitation is in the form of precipitation from MeOH w/$H_2O$ In one embodiment, the organic solvent is not ethanol. In one embodiment the air-drying temperature is about 15° C. to about 25° C., or any temperature or range therein between.

One embodiment is a method of making the anhydrous treprostinil form C by exposing the treprostinil monohydrate Form A and/or Form B to low humidity and/or vacuum at a temperature of less than 42° C. It is understood that the temperature must be less than 42° C., but sufficient to allow the monohydrate's water to evaporate under the applied atmospheric pressure.

The invention will now be described in reference to the following Examples. These examples are not to be regarded a limiting the scope of the present invention, but shall only serve in an illustrative manner.

EXAMPLES

Materials

Materials were used as-received and solvents were either HPLC grade or ACS grade, unless stated otherwise. The treprostinil starting material was received cold and stored under refrigerated conditions. The solid was generally allowed to warm to ambient temperature prior to use. Generated samples were generally stored at ambient temperature.

Preparation of Form a Monohydrate

Treprostinil (500 mg; 1.3 mmol) and 1,4-dioxane/water 1:1 v/v (3.0 mL) were charged to a glass vial. The mixture was agitated, generating homogeneous slurry. The slurry was left to rotate on a wheel at ambient temperature. After approximately 3 days, the slurry was transferred to filter paper in a laboratory fume hood to isolate the solid, spreading the resulting paste thin to aid in drying. Drying was continued on weigh paper, spreading the sample thin, gently breaking up and crushing the solid as it dried. The solid, which seemed dry, was gently crushed and transferred to a clean glass vial. The vial was covered with perforated aluminum foil and left in a laboratory fume hood for approximately 20 hours to complete drying of the solid. Weight loss during drying was approximately 0.9%. The white solid consisted of birefringent blades and needles. Solid recovery was 373 mg. Experimental yield was approximately 71%, accounting for 4.62% water in the solid.

TABLE 1

Observed Peaks for X-ray Powder Diffraction Pattern of Treprostinil monohydrate Form A

| °2θ | d space (Å) | Intensity (%) |
|---|---|---|
| 5.17 ± 0.20 | 17.108 ± 0.689 | 73 |
| 5.88 ± 0.20 | 15.021 ± 0.528 | 9 |
| 7.61 ± 0.20 | 11.624 ± 0.313 | 6 |
| 8.07 ± 0.20 | 10.952 ± 0.278 | 3 |
| 10.36 ± 0.20 | 8.537 ± 0.168 | 91 |
| 11.62 ± 0.20 | 7.618 ± 0.133 | 58 |
| 12.59 ± 0.20 | 7.034 ± 0.113 | 38 |
| 13.15 ± 0.20 | 6.731 ± 0.103 | 12 |
| 15.24 ± 0.20 | 5.813 ± 0.077 | 12 |
| 15.56 ± 0.20 | 5.695 ± 0.074 | 6 |
| 16.18 ± 0.20 | 5.479 ± 0.068 | 36 |
| 17.73 ± 0.20 | 5.002 ± 0.057 | 2 |
| 18.17 ± 0.20 | 4.883 ± 0.054 | 20 |
| 18.77 ± 0.20 | 4.728 ± 0.050 | 7 |
| 19.00 ± 0.20 | 4.670 ± 0.049 | 1 |
| 19.95 ± 0.20 | 4.450 ± 0.045 | 62 |
| 20.12 ± 0.20 | 4.413 ± 0.044 | 40 |
| 20.81 ± 0.20 | 4.269 ± 0.041 | 4 |
| 21.34 ± 0.20 | 4.163 ± 0.039 | 45 |
| 21.59 ± 0.20 | 4.116 ± 0.038 | 74 |
| 21.71 ± 0.20 | 4.094 ± 0.038 | 100 |
| 22.70 ± 0.20 | 3.918 ± 0.034 | 51 |
| 23.06 ± 0.20 | 3.856 ± 0.033 | 32 |
| 23.82 ± 0.20 | 3.736 ± 0.031 | 16 |
| 24.37 ± 0.20 | 3.653 ± 0.030 | 2 |
| 24.63 ± 0.20 | 3.614 ± 0.029 | 18 |

TABLE 1-continued

Observed Peaks for X-ray Powder Diffraction Pattern of Treprostinil monohydrate Form A

| °2θ | d space (Å) | Intensity (%) |
|---|---|---|
| 24.82 ± 0.20 | 3.588 ± 0.029 | 27 |
| 25.49 ± 0.20 | 3.495 ± 0.027 | 2 |
| 26.09 ± 0.20 | 3.416 ± 0.026 | 21 |
| 26.49 ± 0.20 | 3.365 ± 0.025 | 2 |
| 26.87 ± 0.20 | 3.318 ± 0.024 | 1 |
| 27.14 ± 0.20 | 3.286 ± 0.024 | 1 |
| 27.48 ± 0.20 | 3.246 ± 0.023 | 2 |
| 27.68 ± 0.20 | 3.223 ± 0.023 | 3 |
| 28.29 ± 0.20 | 3.154 ± 0.022 | 13 |
| 28.63 ± 0.20 | 3.118 ± 0.021 | 5 |
| 28.88 ± 0.20 | 3.092 ± 0.021 | 3 |

TABLE 2

Characterization of Treprostinil monohydrate Form A Monohydrate

| Analysis | Result |
|---|---|
| single crystal X-ray | Form A structure monohydrate |
| XRPD | Form A indexed |
| DSC | endo 63° C., 49° C. onset |
| | endo 78° C. |
| | endo 119° C. |
| | endo 126° C. |
| TGA | 59° C. onset 4.4 wt % loss to 100° C. |
| hot stage | 26.6° C.; started heating 10° C./min |
| microscopy | 54.8° C.; image suggests liquid present |
| | 62.2° C.; loss of birefringence |
| | 82.3° C.; completely lost birefringence |
| | 121.5° C.; appeared to be crystallizing |
| | 126.6° C.; liquefaction |
| | 147.8° C.; started cooling |
| | 29.4° C.; no crystallization |
| IR | spectrum acquired |
| Raman | spectrum acquired |
| $^1$H-NMR | consistent with structure trace dioxane |
| XRPD | Form A |
| DVS | 0.7% weight gain 5 to 95% RH |
| | 0.6% weight loss 95 to 5% RH |
| XRPD | Form A |
| TG-IR | TG: 4.2 wt % loss to 97° C. |
| (25-97° C.) | IR: volatile identified as water |
| Post-TG-IR XRPD | mesophase |
| XRPD | Form A |
| KF | 4.62% water |
| $^{13}$C-NMR | spectrum acquired |

Single-Crystal Analysis of Form A

The crystals were prepared via elevated temperature (~80° C.) slurry of treprostinil in 1,4-dioxane/water (~1:2.5 v/v) overnight. Crystals were isolated from this sample in Paratone-N oil for single crystal X-ray submission.

A colorless needle of $C_{23}H_{36}O_6$ [$C_{23}H_{34}O_5$, $H_2O$] having approximate dimensions of 0.20 ×0.08×0.06 mm, was mounted on a fiber in random orientation. Preliminary examination and data collection were performed with Cu K$_\alpha$ radiation (λ=1.54184 Å) on a Rigaku Rapid II diffractometer equipped with confocal optics. Refinements were performed using SHELX97 Sheldrick, G. M. *Acta Cryst.*, 2008, A64, 112.

Cell constants and an orientation matrix for data collection were obtained from least-squares refinement using the setting angles of 10698 reflections in the range 3°<θ<66°. The refined mosaicity from CrystalClear is 1.25° indicating poor crystal quality. CrystalClear: *An Integrated Program for the Collection and Processing of Area Detector Data*, Rigaku Corporation, © 1997-2002. The space group was determined by the program XPREP. Bruker, XPREP in SHELXTL v. 6.12, Bruker AXS Inc., Madison, Wis., USA, 2002. From the systematic presence of the following conditions: hkl h+k=2n, and from subsequent least-squares refinement, the space group was determined to be C2 (no. 5).

The data were collected to a maximum 2θ value of 133.14°, at a temperature of 150±1 K.

Frames were integrated with CrystalClear. A total of 10698 reflections were collected, of which 3963 were unique. Lorentz and polarization corrections were applied to the data. The linear absorption coefficient is 0.686 mm$^{-1}$ for Cu K$_\alpha$ radiation. An empirical absorption correction using CrystalClear was applied. Transmission coefficients ranged from 0.858 to 0.960. A secondary extinction correction was applied [1]. The final coefficient, refined in least-squares, was 0.00320 (in absolute units). Intensities of equivalent reflections were averaged. The agreement factor for the averaging was 5.42% based on intensity.

The structure was solved using the Patterson heavy-atom method which revealed the position of one O atom. The remaining atoms were located in succeeding difference Fourier syntheses. Hydrogen atoms residing on oxygen atoms were refined independently. All other hydrogen atoms were included in the refinement but restrained to ride on the atom to which they are bonded. The structure was refined in full-matrix least-squares by minimizing the function:

$$\Sigma w(|F_o|^2 - |F_c|^2)^2$$

The weight w is defined as $1/[\sigma^2(F_o^2) + (0.0478P)^2 + (1.5389P)]$, where $P=(F_o^2 + 2F_c^2)/3$.

Scattering factors were taken from the "International Tables for Crystallography." International Tables for Crystallography, Vol. C, Kluwer Academic Publishers: Dordrecht, The Netherlands, 1992, Tables 4.2.6.8 and 6.1.1.4. Of the 3963 reflections used in the refinements, only the reflections with $F_o^2 > 2\sigma(F_o^2)$ were used in calculating the fit residual, R. A total of 2595 reflections were used in the calculation. The final cycle of refinement included 284 variable parameters and converged (largest parameter shift was <0.01 times its estimated standard deviation) with unweighted and weighted agreement factors of:

$$R = \Sigma|F_o - F_c|/\Sigma F_o = 0.056$$

$$R_w = \sqrt{(\Sigma w(F_o^2 - F_c^2)^2 / \Sigma w(F_o^2)^2)} = 0.119$$

The standard deviation of an observation of unit weight (goodness of fit) was 1.153. The highest peak in the final difference Fourier had a height of 0.25 e/Å$^3$. The minimum negative peak had a height of −0.26 e/Å$^3$. The Flack factor for the determination of the absolute structure refined to 0.3(4). Flack, H. D. *Acta Cryst.* 1983, A39, 876.

The ORTEP diagram was prepared using the ORTEP III (Johnson, C. K. ORTEPIII, Report ORNL-6895, Oak Ridge National Laboratory, TN, U.S.A. 1996. OPTEP-3 for Windows V1.05, Farrugia, L. J., *J. Appl. Cryst.* 1997, 30, 565) program within the PLATON software package. Spek, A. L. *PLATON. Molecular Graphics Program.* Utrecht University, Utrecht, The Netherlands, 2008. Spek, A. L, *J. Appl. Cryst.* 2003, 36, 7. Atoms are represented by 50% probability anisotropic thermal ellipsoids. Packing diagrams were prepared using CAMERON modeling software. Watkin, D. J.; Prout, C. K.; Pearce, L. J. CAMERON, Chemical Crystallography Laboratory, University of Oxford, Oxford, 1996. Assessment of chiral centers was performed with the PLATON software package. Absolute configuration is evaluated using the specification of molecular chirality rules. See, e.g., Cahn, R. S.; Ingold, C; Prelog, V. Angew. *Chem. Intern. Ed. Eng.*, 1966, 5, 385 and Prelog, V. G. Helmchen. Angew. *Chem. Intern. Ed. Eng.*, 1982, 21, 567. Additional figures were generated with the Mercury 3.0 visualization package. Macrae, C. F. Edgington, P. R. McCabe, P. Pidcock, E. Shields, G. P. Taylor, R. Towler M. and van de Streek, J.; *J. Appl. Cryst.*, 2006, 39, 453-457. Hydrogen bonding is represented as dashed lines.

The monoclinic cell parameters and calculated volume are: a=30.213(5) Å, b=4.4372(6) Å, c=22.079(4) Å, α=90.00°, β=129.545(9°), γ=90.00°, V=2282.4(6) Å$^3$. The formula weight of the asymmetric unit in the crystal structure of treprostinil monohydrate Form A is 408.54 g mol$^{-1}$ with Z=4, resulting in a calculated density of 1.189 g cm$^{-3}$. The space group was determined to be C2. The space group and unit cell parameters are in agreement with those determined previously for Form A from XRPD indexing.

The quality of the structure obtained is high, as indicated by the fit residual, R of 0.056 (5.6%). R-values in the range of 0.02 to 0.06 are quoted for the most reliably determined structures. Glusker, Jenny Pickworth; Trueblood, Kenneth N. *Crystal Structure Analysis: A Primer*, 2$^{nd}$ ed.; Oxford University press: New York, 1985; p. 87.

Figure 18:
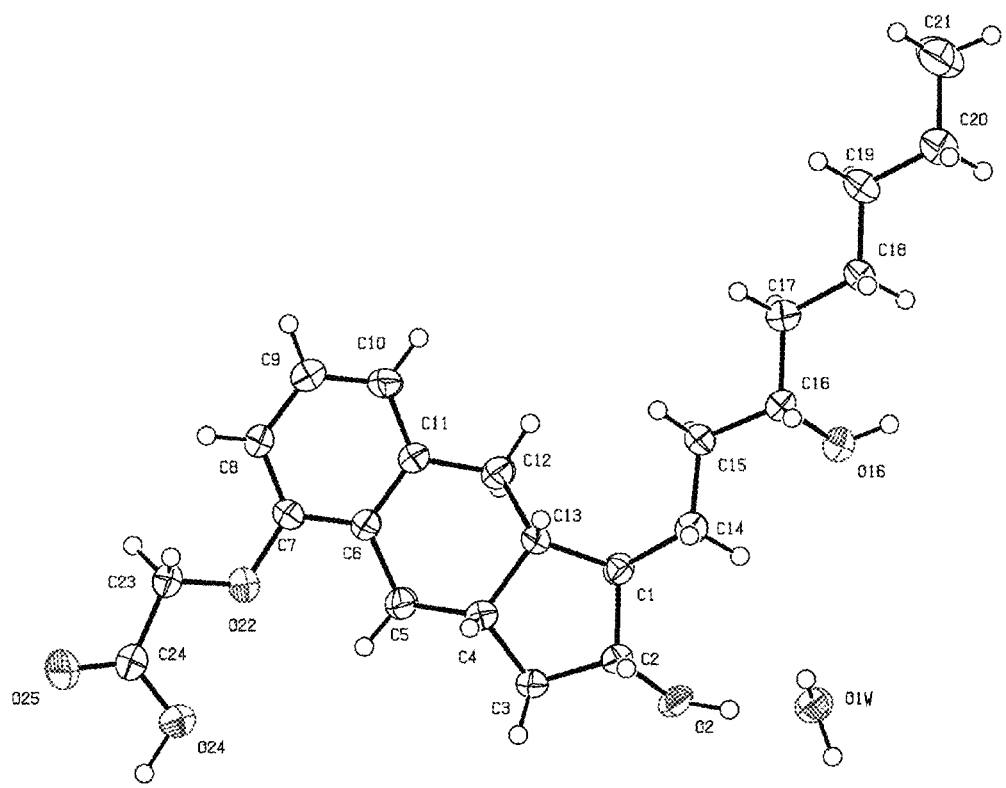
FIG. 18 is an ORTEP drawing of treprostinil monohydrate Form A. Atoms are represented by 50% probability anisotropic thermal ellipsoids.
Figure 19:
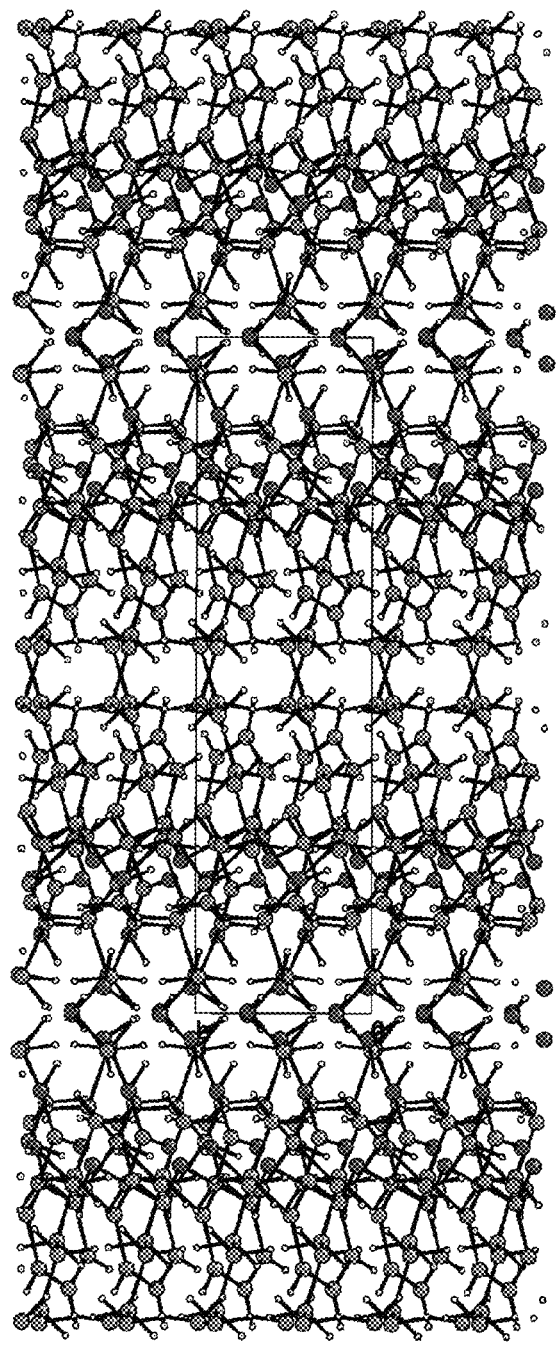
FIG. 19 is a packing diagram of treprostinil monohydrate Form A viewed down the crystallographic a axis.
Figure 20:
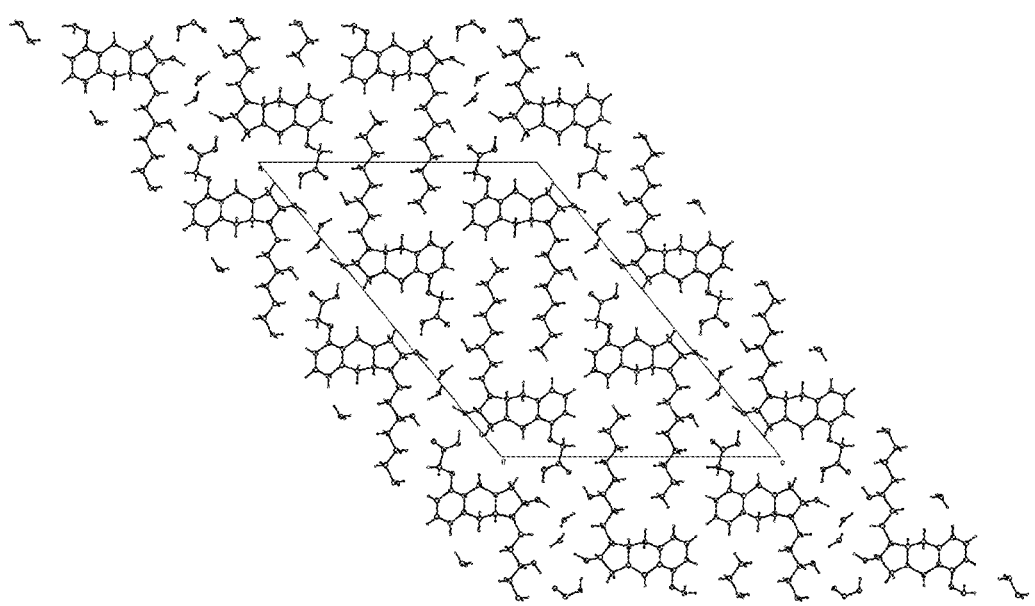
FIG. 20 is a packing diagram of treprostinil monohydrate Form A viewed down the crystallographic b axis.
Figure 21:
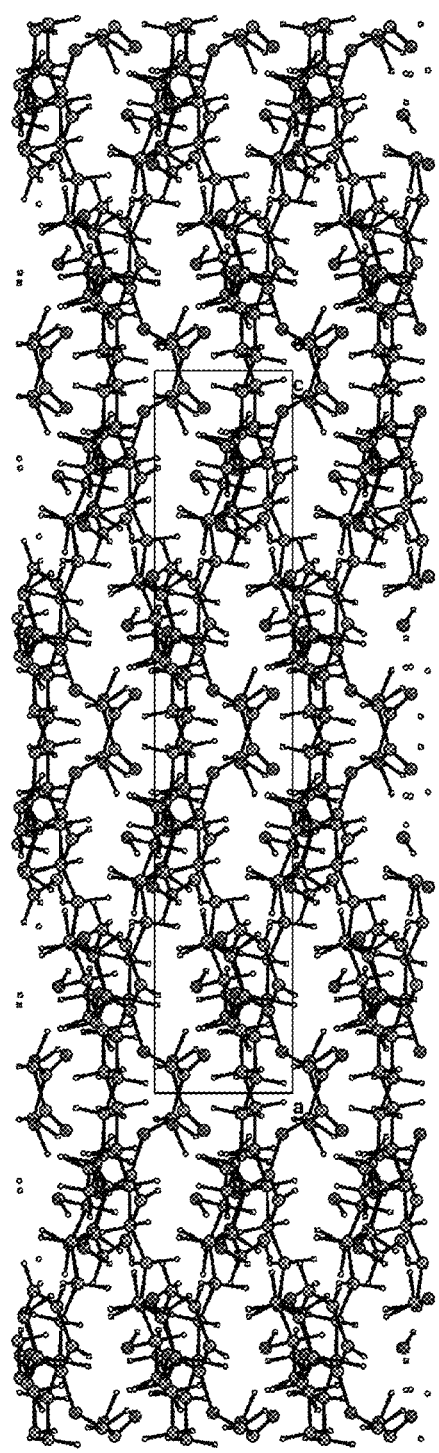
FIG. 21 is a packing diagram of treprostinil monohydrate Form A viewed down the crystallographic c axis.
Figure 22:
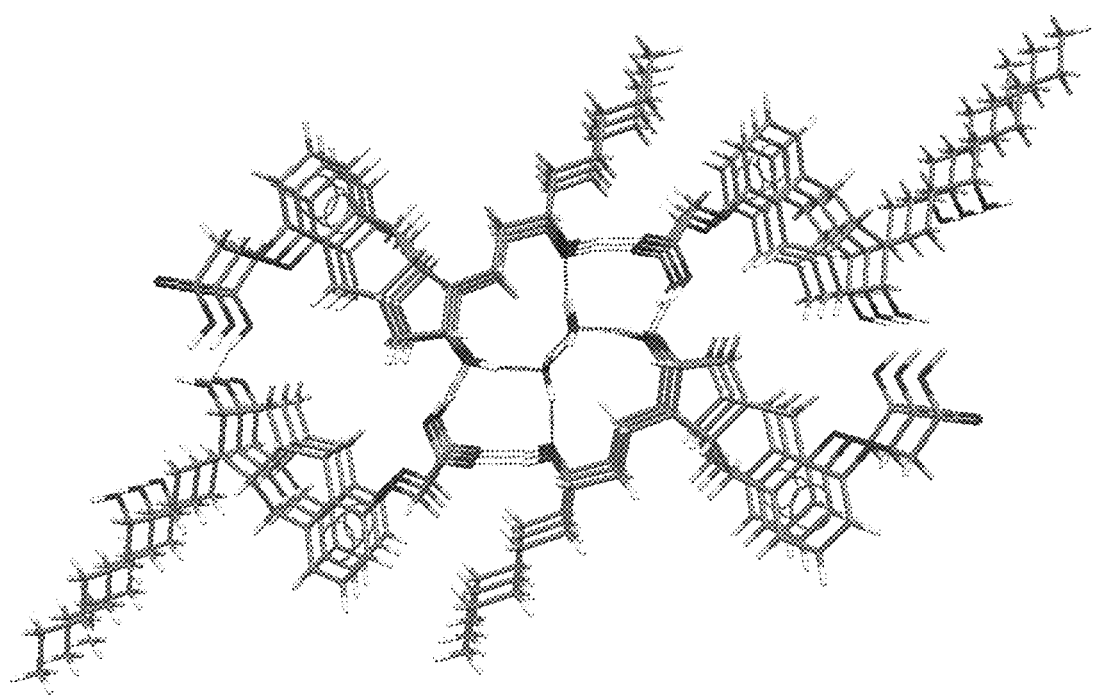
FIG. 22 is hydrogen bonded tunnels in treprostinil monohydrate Form A down the b axis.
Figure 23:
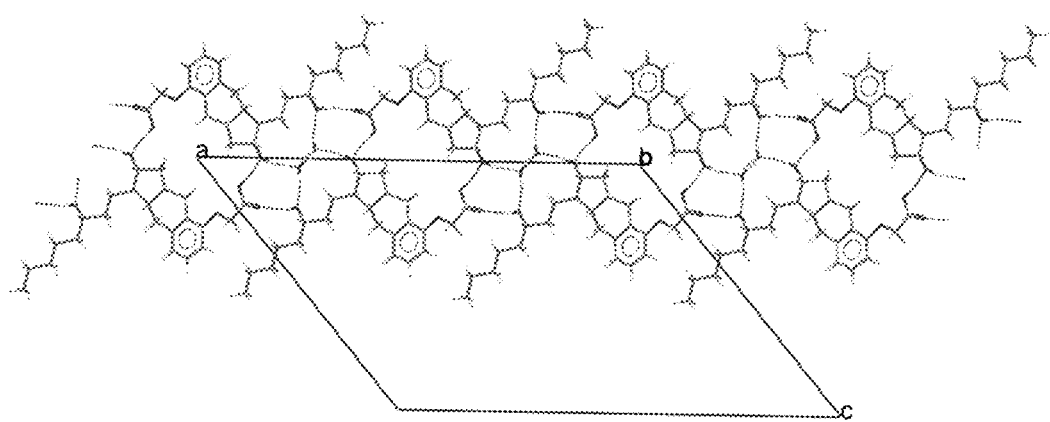
FIG. 23 is hydrogen bonding along the a axis in treprostinil monohydrate Form A.
Figure 24:
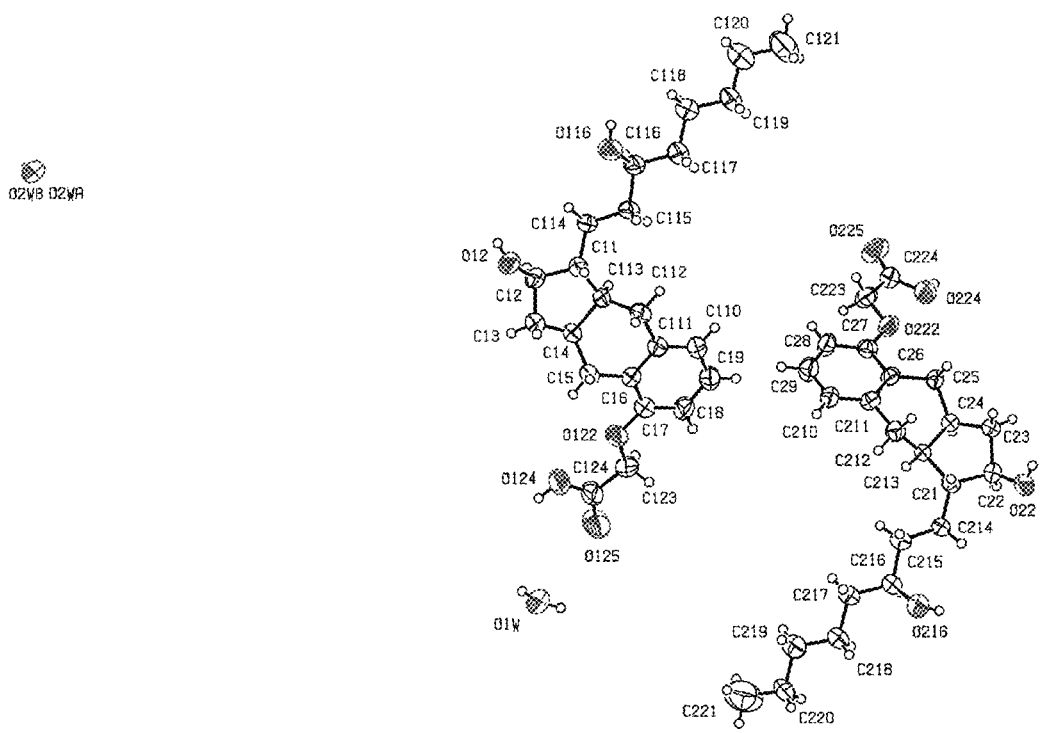
FIG. 24 is an ORTEP drawing of treprostinil monohydrate Form B. Atoms are represented by 50% probability anisotropic thermal ellipsoids.
Figure 25:
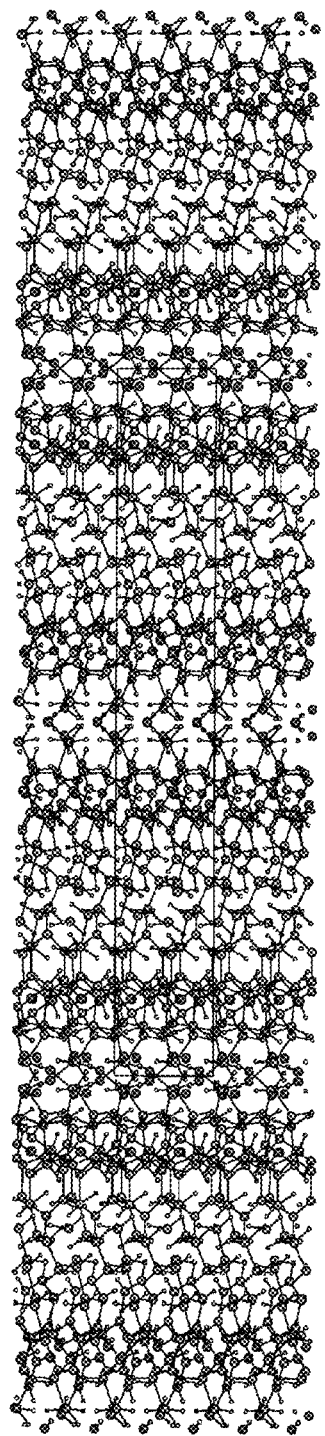
FIG. 25 v diagram of treprostinil monohydrate Form B viewed down the crystallographic a axis.
Figure 26:
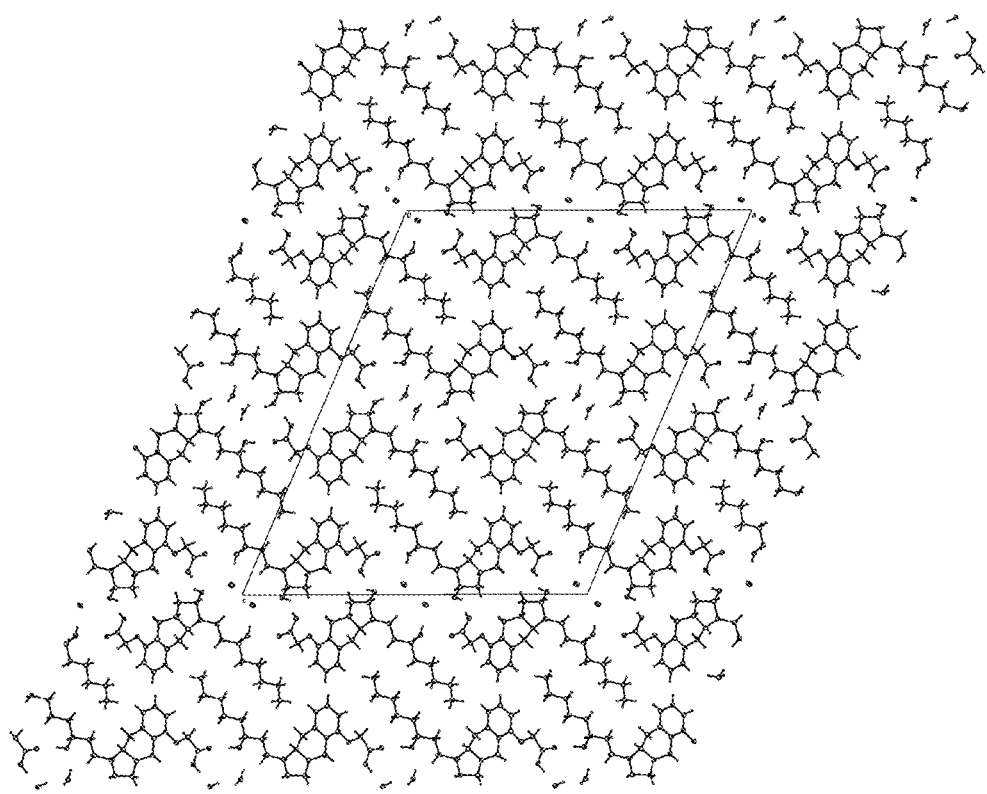
FIG. 26 is a packing diagram of treprostinil monohydrate Form B viewed down the crystallographic b axis.
Figure 27:
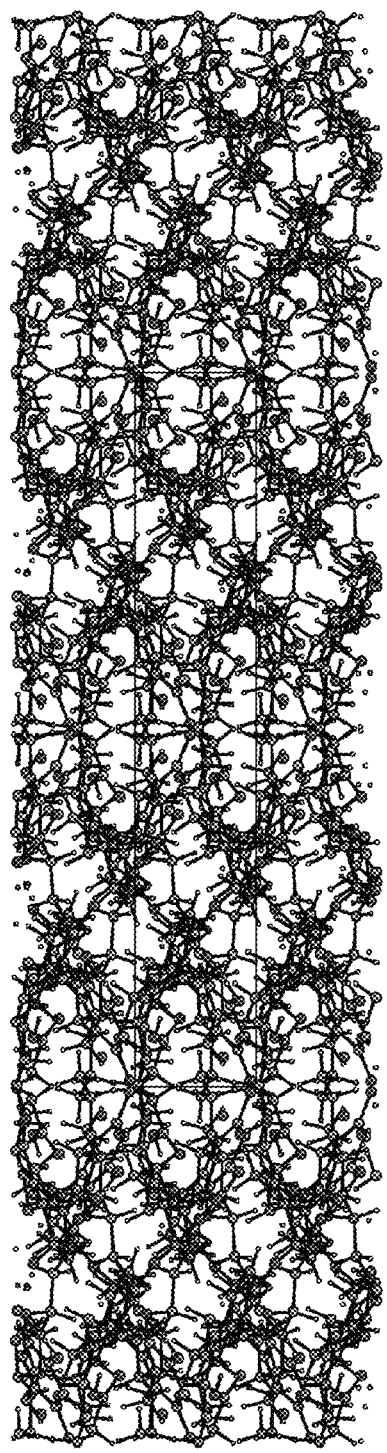
FIG. 27 is a packing diagram of treprostinil monohydrate Form B viewed down the crystallographic c axis.
Figure 28:
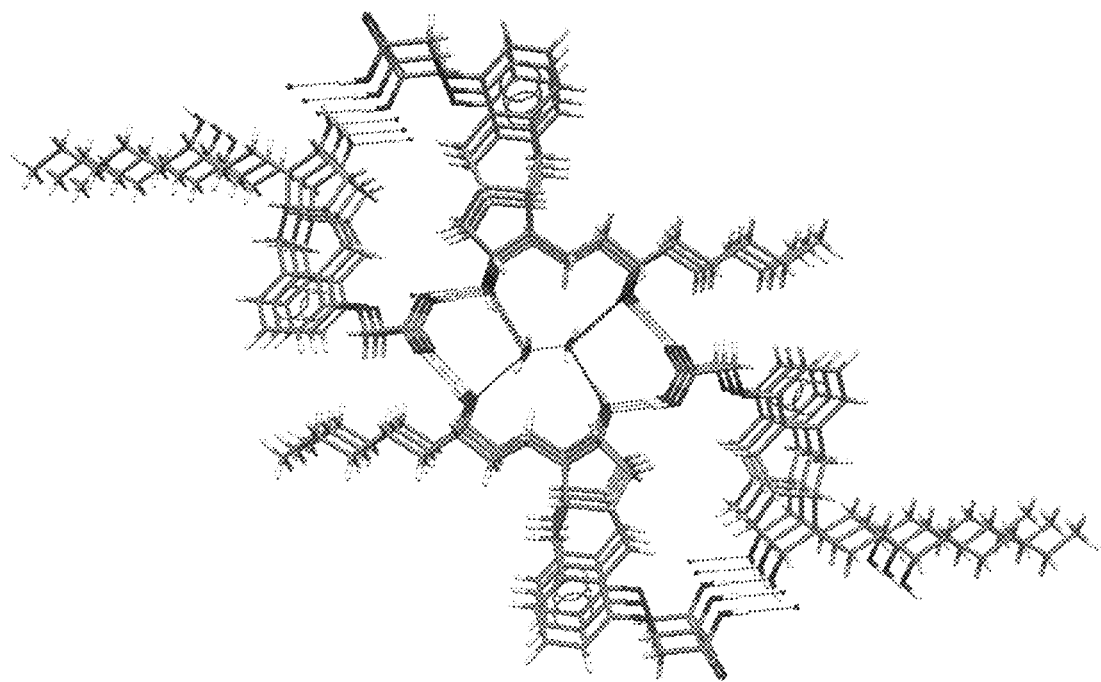
FIG. 28 is hydrogen bonded helix down the b axis of treprostinil monohydrate Form B.
Figure 29:
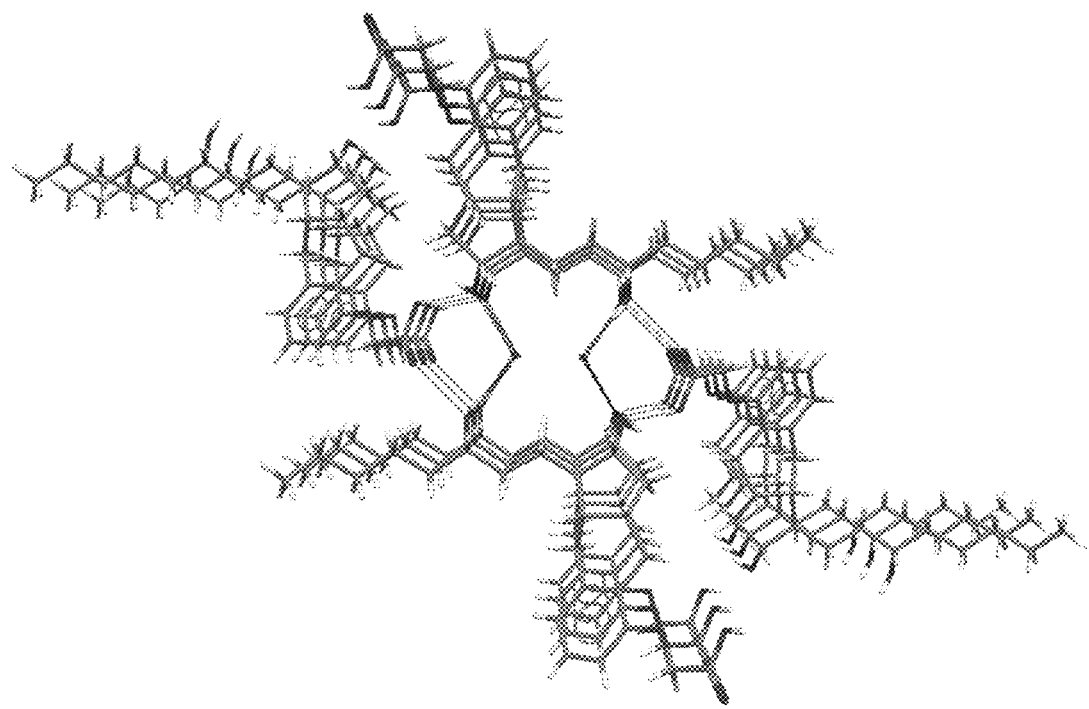
FIG. 29 is a hydrogen-bonded tetramer that does not repeat along the b axis by hydrogen bonding between the molecules of treprostinil monohydrate Form B.
Figure 30:
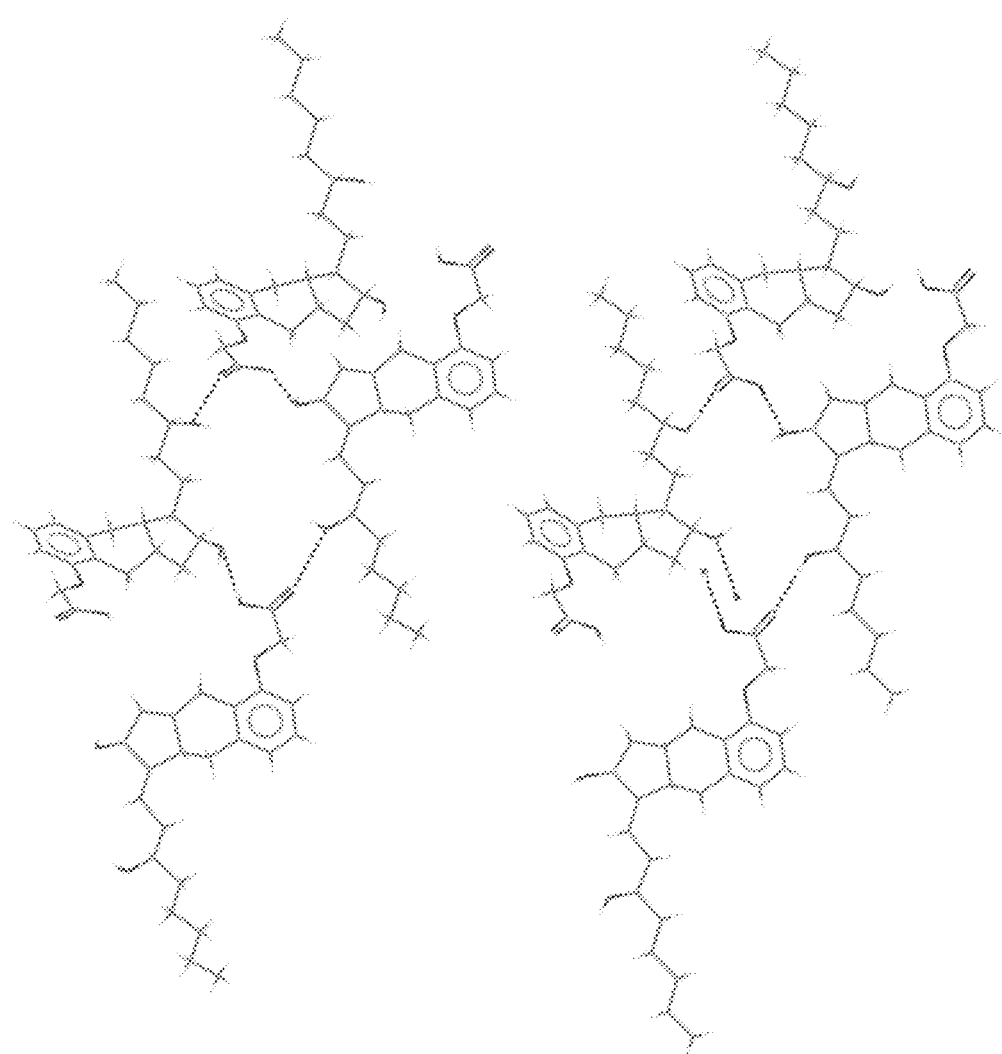
FIG. 30 is a comparison of the two-hydrogen bonding motifs formed by the treprostinil molecules. Water is not shown for clarity. Closed tetramer is shown on the left and open helix is shown on the right.

An ORTEP drawing of treprostinil monohydrate Form A is shown in FIG. 18. The molecule observed in the asymmetric unit of the single crystal structure is consistent with the proposed molecular structure provided in herein. The asymmetric unit shown in FIGS. 19 to 23 contains one treprostinil molecule for every one water molecule, indicating that Form A is a monohydrate.

The single crystal structure of treprostinil was determined to confirm the molecular structure and the observed absolute configuration is consistent with the proposed absolute configuration. The structure of treprostinil was determined to be a monohydrated crystal form, designated Form A. The crystal structure contains one treprostinil molecule and one water molecule in the asymmetric unit.

Preparation of Form B Monohydrate

Treprostinil (1019 mg; 2.6 mmol) and methanol (3.5 mL) were charged to a glass vial. The mixture was agitated and sonicated, generating a clear solution. The solution was filtered to a clean glass vial and combined with water (3.5 mL), resulting in solid slurry. The vial was capped and left at ambient temperature. After approximately 3 days, the resulting thick paste was transferred to filter paper in a laboratory fume hood to isolate the solid, spreading thin to aid in drying. Drying was continued on weigh paper, spreading the sample thin, gently breaking up and crushing the solid as it dried. The solid, which seemed damp, was gently crushed and transferred to a clean glass vial. The vial was left in a laboratory fume hood for approximately 44 hours to complete drying of the solid, periodically breaking up and crushing the solid to aid in drying. Drying was done with and without a perforated aluminum foil cover on the vial. Weight loss during drying was approximately 32.4%. The white solid consisted of birefringent needles in dendritic-rosette clusters. Solid recovery was 956 mg. Experimental yield was approximately 82%, accounting for 12.24% water in the solid. The solid formed hard chunks during slurry and drying.

In a similar procedure to the single-crystal determination for Form A, Form B was determined.

Frames were integrated with CrystalClear. A total of 21922 reflections were collected, of which 7134 were unique. Lorentz and polarization corrections were applied to the data. The linear absorption coefficient is 0.683 mm$^{-1}$ for Cu K$_\alpha$ radiation. An empirical absorption correction using CrystalClear was applied. Transmission coefficients ranged from 0.837 to 0.986. A secondary extinction correction was applied [1]. The final coefficient, refined in least-squares, was 0.000370 (in absolute units). Intensities of equivalent reflections were averaged. The agreement factor for the averaging was 5.76% based on intensity.

The structure was solved using the Patterson heavy-atom method which revealed the position of one O atom. The remaining atoms were located in succeeding difference Fourier syntheses. Some of the hydrogen atoms were refined independently, though the majority of the hydrogen atoms were included in the refinement but restrained to ride on the atom to which they are bonded. The structure was refined in full-matrix least-squares by minimizing the function:

$$\Sigma w(|F_o|^2-|F_c|^2)^2$$

The weight w is defined as $1/[\sigma^2(F_o^2)+(0.0589P)^2+(3.3421P)]$, where $P=(F_o^2+2F_c^2)/3$.

Scattering factors were taken from the "International Tables for Crystallography". Of the 7134 reflections used in the refinements, only the reflections with $F_o^2>2\sigma(F_o^2)$ were used in calculating the fit residual, R. A total of 3905 reflections were used in the calculation. The final cycle of refinement included 551 variable parameters and converged (largest parameter shift was <0.01 times its estimated standard deviation) with unweighted and weighted agreement factors of:

$$R=\Sigma|F_o-F_c|/\Sigma F_o=0.068$$

$$R_w = \sqrt{(\sum w(F_o^2 - F_c^2)^2 / \sum w(F_o^2)^2)} = 0.135$$

The standard deviation of an observation of unit weight (goodness of fit) was 1.063. The highest peak in the final difference Fourier had a height of 0.28 e/Å$^3$. The minimum negative peak had a height of −0.22 e/Å$^3$. The Flack factor for the determination of the absolute structure refined to 0.0(4).

The monoclinic cell parameters and calculated volume are: a=29.8234(8) Å, b=4.63510(10) Å, c=36.126(3) Å, α=90.00°, □β=113.334(8°), γ=90.00°, V=4585.5(4) Å$^3$. The formula weight of the asymmetric unit in the crystal structure of treprostinil monohydrate Form B is 407.53 g mol$^{-1}$ with Z=8, resulting in a calculated density of 1.181 g cm$^{-3}$. The space group was determined to be C2. The space group and unit cell parameters are in agreement with those obtained previously from XRPD indexing.

The quality of the structure obtained is moderate, as indicated by the fit residual, R of 0.068 (6.8%). R-values in the range of 0.02 to 0.06 are quoted for the most reliably determined structures. See, e.g., Glusker, Jenny Pickworth; Trueblood, Kenneth N. *Crystal Structure Analysis: A Primer*, 2$^{nd}$ ed.; Oxford University press: New York, 1985; p. 87. While the overall quality of the structure falls outside of the standard range, the data was sufficient to determine the molecular conformation of the treprostinil molecule and the contents of the asymmetric unit.

The single crystal structure of treprostinil was determined to confirm the molecular structure and the observed absolute configuration is consistent with that of the proposed molecular structure. The structure of treprostinil was determined to be a monohydrated crystal form, designated Form B. The crystal structure contains two treprostinil molecules and two water molecules in the asymmetric unit. The absolute structure was determined from the crystal structure to most likely be R,R,S,S, and S configuration at C11 (C21), C12 (C22), C14 (C24), C113 (C213), and C116 (C216), respectively. All peaks in the experimental pattern are represented in the calculated XRPD pattern, indicating the bulk material is likely a single phase.

TABLE 3

Observed Peaks for X-ray Powder Diffraction Pattern of Treprostinil monohydrate Form B

| °2θ | d space (Å) | Intensity (%) |
| --- | --- | --- |
| 2.66 ± 0.20 | 33.230 ± 2.702 | 3 |
| 5.32 ± 0.20 | 16.625 ± 0.649 | 53 |
| 5.92 ± 0.20 | 14.936 ± 0.522 | 33 |
| 6.44 ± 0.20 | 13.735 ± 0.440 | 12 |
| 8.02 ± 0.20 | 11.020 ± 0.281 | 1 |
| 9.86 ± 0.20 | 8.970 ± 0.185 | 3 |
| 10.66 ± 0.20 | 8.297 ± 0.158 | 54 |
| 12.10 ± 0.20 | 7.314 ± 0.122 | 38 |
| 12.90 ± 0.20 | 6.861 ± 0.108 | 35 |
| 13.10 ± 0.20 | 6.757 ± 0.104 | 19 |
| 15.81 ± 0.20 | 5.605 ± 0.071 | 13 |
| 16.13 ± 0.20 | 5.496 ± 0.069 | 27 |
| 16.96 ± 0.20 | 5.227 ± 0.062 | 2 |
| 17.21 ± 0.20 | 5.151 ± 0.060 | 1 |
| 17.83 ± 0.20 | 4.974 ± 0.056 | 3 |
| 18.07 ± 0.20 | 4.910 ± 0.055 | 1 |
| 18.52 ± 0.20 | 4.792 ± 0.052 | 22 |
| 18.72 ± 0.20 | 4.741 ± 0.051 | 12 |
| 19.45 ± 0.20 | 4.563 ± 0.047 | 48 |
| 19.80 ± 0.20 | 4.483 ± 0.045 | 29 |
| 20.17 ± 0.20 | 4.402 ± 0.044 | 29 |
| 20.56 ± 0.20 | 4.321 ± 0.042 | 65 |
| 20.99 ± 0.20 | 4.232 ± 0.040 | 12 |
| 21.22 ± 0.20 | 4.186 ± 0.039 | 37 |
| 21.56 ± 0.20 | 4.122 ± 0.038 | 100 |
| 22.26 ± 0.20 | 3.994 ± 0.036 | 62 |
| 22.91 ± 0.20 | 3.881 ± 0.034 | 9 |
| 23.10 ± 0.20 | 3.851 ± 0.033 | 27 |
| 23.85 ± 0.20 | 3.731 ± 0.031 | 7 |
| 24.38 ± 0.20 | 3.651 ± 0.030 | 53 |
| 24.60 ± 0.20 | 3.619 ± 0.029 | 26 |
| 25.19 ± 0.20 | 3.536 ± 0.028 | 17 |
| 25.34 ± 0.20 | 3.515 ± 0.028 | 10 |
| 26.00 ± 0.20 | 3.427 ± 0.026 | 10 |
| 26.39 ± 0.20 | 3.378 ± 0.025 | 3 |
| 26.86 ± 0.20 | 3.320 ± 0.024 | 4 |
| 27.09 ± 0.20 | 3.292 ± 0.024 | 5 |
| 27.39 ± 0.20 | 3.256 ± 0.023 | 6 |
| 27.66 ± 0.20 | 3.225 ± 0.023 | 2 |
| 28.48 ± 0.20 | 3.134 ± 0.022 | 11 |
| 28.68 ± 0.20 | 3.113 ± 0.021 | 6 |
| 29.16 ± 0.20 | 3.062 ± 0.021 | 5 |
| 29.36 ± 0.20 | 3.042 ± 0.020 | 6 |

TABLE 4

Characterization of Treprostinil monohydrate Form B Monohydrate

| Analysis | Result |
| --- | --- |
| single crystal X-ray | Form B structure monohydrate |
| XRPD | Form B indexed |
| $^1$H-NMR | consistent with structure |
| XRPD | Form B |
| Raman | spectrum acquired |
| XRPD | Form B |
| DSC | endo 61° C., 48° C. onset |
| | endo 75° C. |
| | endo 118° C. |
| | endo 125° C. |

TABLE 4-continued

Characterization of Treprostinil monohydrate Form B Monohydrate

| Analysis | Result |
|---|---|
| TGA | 58° C. onset 4.4 wt % loss to 100° C. |
| IR | spectrum acquired |
| DVS | 0.3% weight gain upon equilibration at 55% RH |
| | 0.4% weight gain 55 to 95% RH |
| | 0.6% weight loss 95 to 5% RH |
| XRPD | Form B |
| KF | 12.24% water |
| $^{13}$C-NMR | spectrum acquired |

Preparation of Form C Dehydrate

Treprostinil monohydrate Form B (521 mg) was charged to a glass vial. The vial was covered with a filter and exposed to vacuum at ambient temperature for approximately 20 hours to dry the solid. Weight loss during drying was approximately 15.7%. The resulting solid was white and contained 0.0% water. Solid recovery was 439 mg.

TABLE 5

Observed Peaks for XRPD of Treprostinil Form C

| °2θ | d space (Å) | Intensity (%) |
|---|---|---|
| 3.06 ± 0.20 | 28.876 ± 2.019 | 2 |
| 4.36 ± 0.20 | 20.252 ± 0.972 | 1 |
| 6.55 ± 0.20 | 13.490 ± 0.424 | 100 |
| 11.78 ± 0.20 | 7.511 ± 0.129 | 6 |
| 12.13 ± 0.20 | 7.294 ± 0.122 | 7 |
| 12.55 ± 0.20 | 7.052 ± 0.114 | 17 |
| 13.17 ± 0.20 | 6.723 ± 0.103 | 20 |
| 14.76 ± 0.20 | 6.003 ± 0.082 | 2 |
| 17.33 ± 0.20 | 5.117 ± 0.059 | 7 |
| 17.98 ± 0.20 | 4.933 ± 0.055 | 16 |
| 18.27 ± 0.20 | 4.857 ± 0.053 | 9 |
| 18.74 ± 0.20 | 4.736 ± 0.051 | 6 |
| 19.64 ± 0.20 | 4.521 ± 0.046 | 20 |
| 20.04 ± 0.20 | 4.431 ± 0.044 | 26 |
| 20.71 ± 0.20 | 4.290 ± 0.041 | 45 |
| 21.41 ± 0.20 | 4.151 ± 0.039 | 12 |
| 22.60 ± 0.20 | 3.935 ± 0.035 | 2 |
| 23.16 ± 0.20 | 3.840 ± 0.033 | 3 |
| 23.60 ± 0.20 | 3.770 ± 0.032 | 3 |
| 25.19 ± 0.20 | 3.536 ± 0.028 | 10 |
| 25.95 ± 0.20 | 3.433 ± 0.026 | 1 |
| 27.51 ± 0.20 | 3.243 ± 0.023 | 1 |
| 29.20 ± 0.20 | 3.059 ± 0.021 | 2 |

TABLE 6

Characterization of Treprostinil Form C Dehydrate

| Analysis | Result |
|---|---|
| XRPD | Form C |
| DSC | endo 95° C., 90° C. onset |
| | endo 119° C. |
| | endo 126° C. |
| TGA | 0.2 wt % loss to 100° C. |
| hot stage | 25.2° C.; started heating 10° C./min |
| microscopy | 97.0° C.; change in birefringence, possible recrystallization |
| | 104.7° C.; started cooling 10° C./min |
| | 75.3° C.; no change; started heating 10° C./min |
| | 115.7° C.; started heating 2° C./min |
| | 119.1° C.; appeared to be growth of irregular acicular-shaped particles; started heating 10° C./min |
| | 124.1° C.; liquefaction onset |
| IR | spectrum acquired |
| Raman | spectrum acquired |
| $^1$H-NMR | consistent with structure weak unknown peak at 0.07 ppm |

TABLE 6-continued

Characterization of Treprostinil Form C Dehydrate

| Analysis | Result |
|---|---|
| DVS | 0.1% weight loss upon equilibration at 5% RH |
| | 0.2% weight gain 5 to 75% RH |
| | 4.6% weight gain 75 to 95% RH |
| | 0.5% weight loss 95 to 5% RH |
| post-DVS XRPD | B + A |
| XRPD | Form C |
| KF | 0.00% water |
| $^{13}$C-NMR | spectrum acquired |

Experimental Methods

Approximate Solubility

Solubility was estimated by a solvent addition method in which a weighed sample was treated with aliquots of the test solvent. The mixture was generally vortexed and/or sonicated between additions to facilitate dissolution. Complete dissolution of the test material was determined by visual inspection. Solubility was estimated based on the total solvent used to provide complete dissolution. The actual solubility may be greater than the value calculated because of the use of solvent aliquots that were too large or due to a slow rate of dissolution. The solubility is expressed as "less than" if dissolution did not occur during the experiment.

Evaporation

Solvents were added to weighed solid in glass vials. Samples were often heated, agitated and/or sonicated to facilitate dissolution. The resulting solutions were filtered into clean vials which were left uncovered (fast evaporation) or with a loose cap (slow evaporation) to evaporate solvents in a laboratory fume hood at ambient or specified stirplate setpoint temperature. Solutions were also rotary evaporated. Samples were taken to dryness unless specified.

Slurry

Mixtures were generated in glass vials so that undissolved solid remained. Samples were agitated on a stirplate at specified setpoint temperature, unless indicated, or on a rotating wheel at ambient temperature. At specified times, samples were removed for examination by PLM and/or solid recovery for XRPD analysis. Solid was generally recovered via vacuum filtration or paste transfer to filter paper, allowing the solid to dry in a laboratory fume hood, unless specified.

Slurries at specific water activities [7,8,9,10] were conducted using acetone, ethanol, isopropanol, and methanol. The slurries were prepared using aqueous solvent mixtures and/or adding water to solid, followed by specified solvents. The slurries were sampled for XRPD at specified times, pipeting into 1.0 mm glass capillaries and concentrating the solid via centrifugation. Prior to the first sampling, solid and/or aqueous solvent mixtures were added to some of the slurries to maintain slurry consistency. The acetone slurry at 0.8 water activity could not be sampled directly into the capillary, so solid was isolated via decantation of the supernatant and partially dried on filter paper in a laboratory fume hood, prior to packing in the capillary.

Slow Cool

For slow cool experiments, solutions were prepared at specified stirplate setpoint temperatures and filtered to clean glass vials. The heat was shut off, allowing the samples to cool slowly to ambient temperature. If precipitation was insufficient, samples were placed under refrigerated conditions. Solid was isolated in the same manner described for slurry.

Crash Cool

For crash cool experiments, solutions were prepared at ambient or specified stirplate setpoint temperature and filtered to clean glass vials. The solutions were cooled rapidly via a cold bath of dry ice and isopropanol, leaving in the bath for at least a few minutes. If precipitation was insufficient, samples were placed under refrigerated conditions. Solid was isolated in the same manner described for slurry.

Crash Precipitation

For crash precipitation experiments, solutions were filtered into glass vials containing a known volume of antisolvent, or aliquots of antisolvent were added to the filtered solutions. If precipitation was insufficient, samples were left at ambient temperature or other specified conditions. Solid was isolated in the same manner described for slurry.

Vapor Diffusion

For vapor diffusion experiments, glass vials containing filtered solutions were exposed to various vapors by placing into larger vials with antisolvent in the bottom.

Milling

Milling was carried out in an agate jar, with agate ball, in a Retsch MM200 mixer mill, using approximately 100 mg of solid. The solid was ground 6 times at 30 Hz, 2 minutes per grind, scraping the solid from the agate after each grind.

Melt/Quench

Solids were heated using a hot plate, Thomas-Hoover capillary melting point apparatus or Wagner & Munz Heizbank system (Kofler Type WME). Heating was continued until all of the solids appeared to have melted. Rapid solidification (quench) of the melt was achieved via removal to a chilled metallic heat sink or ambient-temperature laboratory bench.

The hot plate experiment was done in a glass vial. The heat setting was 130 to 140° C. Solid was scraped down from the vial walls and the vial was slowly rolled to encourage complete liquefaction of the solid. Solidification of the melt occurred quickly as vial surfaces lost contact with the heat.

For the capillary experiment, a 1.0 mm glass capillary was placed inside a slightly larger glass capillary. Upon quench, the material spread around the walls of the capillary, thus the solid packing was no longer dense enough for XRPD. Temperature was measured by a NIST-traceable thermometer.

The Kofler experiment was done on a glass slide, moving the sample across the hot bench to pass the entire solid through approximately 141° C. The hot bench was calibrated using USP melting point standards.

Lyophilization

Solids were dissolved in 1,4-dioxane or 1,4-dioxane/water mixtures. The resulting solutions were filtered and then frozen slowly by freezer or quickly by cold bath of dry ice and isopropanol. The frozen sample was placed under vacuum at approximately −50° C. using an FTSsystems Flexi-Dry freeze dryer.

Environmental Stress

Solids were stressed in glass vials under various drying and relative humidity (RH) environments for specified times, generally monitoring weight change during stressing. Drying was done via ambient, $P_2O_5$, vacuum (ambient and elevated temperatures), and convection oven experiments, for which the only drying condition listed in the tables is the oven temperature. Ambient experiments were conducted by leaving samples exposed in a laboratory fume hood. Specific RH values were achieved by placing the sample inside sealed chambers containing saturated salt solutions or into separate chambers containing $P_2O_5$ powder for 0% RH. The salt solutions were selected and prepared based an ASTM standard procedure. For vacuum experiments, vials were covered with nylon filters to prevent potential solid loss. For the elevated temperature experiments, temperature was measured by a NIST-traceable thermometer. For other stress experiments, vials were covered with perforated aluminum foil or left uncovered. Solids were stored at ambient temperature in sealed vials prior to XRPD analysis.

Polarized Light Microscopy (PLM)

In general, PLM was performed using a Leica MZ12.5 stereomicroscope. Samples were viewed in situ or on a glass slide (generally covered in mineral or Paratone-N oils) with or without crossed polarizers and a first order red compensator using various objectives ranging from 0.8-10x. Crystallinity is indicated by the observance of birefringence and extinction.

For lot 01C10010, PLM was performed using a Leica DM LP microscope equipped with a SPOT Insight™ color digital camera. The sample was placed on a glass slide, a cover glass was placed over the sample, and a drop of mineral oil was added to cover the sample by capillarity. The sample was observed using a 10, 20 and 40☐ objectives with crossed polarizers and a first order red compensator. Images were captured using SPOT software (v. 4.5.9). A micron bar was inserted onto each image as a reference for particle size.

X-ray Powder Diffraction (XRPD)

Inel XRG-3000 Diffractometer

XRPD patterns were collected with an Inel XRG-3000 diffractometer. An incident beam of Cu Kα radiation was produced using a fine-focus tube and a parabolically graded multilayer mirror. Prior to the analysis, a silicon specimen (NIST SRM 640d) was analyzed to verify the observed position of the Si 111 peak is consistent with the NIST-certified position. A specimen of the sample was packed into a thin-walled glass capillary, and a beam-stop was used to minimize the background from air. Diffraction patterns were collected in transmission geometry using Windif v. 6.6 software and a curved position-sensitive Equinox detector with a 2θ range of 120°. The data acquisition parameters for each pattern are displayed above the image in Appendix C; data are displayed 2.5-40°2θ.

PANalytical X'Pert PRO Diffractometer

High resolution XRPD patterns were collected with a PANalytical X'Pert PRO MPD diffractometer using an incident beam of Cu radiation produced using an Optix long, fine-focus source. An elliptically graded multilayer mirror was used to focus Cu Kα X-rays through the specimen and onto the detector. Prior to the analysis, a silicon specimen (NIST SRM 640d) was analyzed to verify the observed position of the Si 111 peak is consistent with the NIST-certified position. A specimen of the sample was sandwiched between 3-µm-thick films and analyzed in transmission geometry. A beam-stop, short antiscatter extension and antiscatter knife edge were used to minimize the background generated by air. Soller slits for the incident and diffracted beams were used to minimize broadening from axial divergence. Diffraction patterns were collected using a scanning position-sensitive detector (X'Celerator) located 240 mm from the specimen and Data Collector software v. 2.2b. The data acquisition parameters for each pattern are displayed above the image in Appendix C including the divergence slit (DS) before the mirror and the incident-beam antiscatter slit (SS); data are displayed 2.5-40°2θ.

XRPD patterns were collected with a PANalytical X'Pert PRO MPD diffractometer using an incident beam of Cu Kα radiation produced using a long, fine-focus source and a nickel filter. The diffractometer was configured using the symmetric Bragg-Brentano geometry. Prior to the analysis, a silicon specimen (NIST SRM 640d) was analyzed to verify the observed position of the Si 111 peak is consistent with the NIST-certified position. A specimen of the sample was prepared as a /thin, circular layer centered on a silicon zero-background substrate. Antiscatter slits (SS) were used to minimize the background generated by air. Soller slits for the incident and diffracted beams were used to minimize broadening from axial divergence. Diffraction patterns were collected using a scanning position-sensitive detector (X'Celerator) located 240 mm from the sample and Data Collector software v. 2.2b. The data acquisition parameters for each pattern are:

Form A: Panalytical X-Pert Pro MPD PW3040 Pro X-ray Tube: Cu(1.54059 A) Voltage: 45 kV Amperage: 40 mA Scan Range: 1.00-39.99°2θ Step Size: 0.017°2θ Collection Time: 719 s Scan Speed: 3.3°/min Slit DS: 112° SS: null Revolution Time: 1.0 s Mode: Transmission Form B: Panalvtical X-Pert Pro MPD PW3040 Pro X-ray Tube: Cu(1.54059 A) Voltage: 45 kV Amperage: 40 mA Scan Range: 1.00-39.99°2θ Step Size: 0.017°2θ Collection Time: 3883 s Scan Speed: 0.6°/min Slit: DS: 1/2° SS: null Revolution Time: 1.0 s Mode: Transmission.

Form C: X-ray Tube: Cu(1.54059 A) Voltage: 45 kV Amperage: 40 mA Scan Range: 1.00-39.99°2θ Step Size: 0.017°2θ Collection Time: 719 s Scan Speed: 3.3°/min Slit: DS: 1/2° SS: null Revolution Time: 1.0 s Mode: Transmission Differential Scanning Calorimetry (DSC)

DSC was performed using TA Instruments 2920 and Q2000 differential scanning calorimeters. Temperature calibration was performed using NIST-traceable indium metal. The sample was placed into an aluminum DSC pan, covered with a lid, and the weight was accurately recorded. A weighed aluminum pan configured as the sample pan was placed on the reference side of the cell. Endotherm temperatures reported are transition maxima unless specified. The data acquisition parameters and pan configuration for each thermogram are displayed in the image in the Figures Section. The method code on the thermogram is an abbreviation for the start and end temperature as well as the heating rate; e.g., −50-250-10 means "from −50° C. to 250° C., at 10° C./min". The following table summarizes the abbreviations used in each image for pan configurations:

| Abbreviation (in comments) | Meaning |
| --- | --- |
| T0 | Tzero, indicates pan has no lip |
| C | Lid crimped |
| MP | manual pinhole |

Thermogravimetric Analysis (TGA)

TG analyses were performed using a TA Instruments Q5000 IR thermogravimetric analyzer. Temperature calibration was performed using nickel and Alumel. Each sample was placed in an aluminum pan. The sample was hermetically sealed, the lid pierced, then inserted into the TG furnace. The furnace was heated under nitrogen. The data acquisition parameters for each thermogram are displayed in the image in the Figures Section. The method code on the thermogram is an abbreviation for the start and end temperature as well as the heating rate; e.g., 00-350-10 means "from current temperature to 350° C., at 10° C./min", that is the temperature was not equilibrated prior to the start of the analysis.

Thermogravimetric Infrared (TG-IR) Spectroscopy

Thermogravimetric infrared (TG-IR) analysis was performed on a TA Instruments thermogravimetric (TG) analyzer model 2050 interfaced to a Magna-IR 560® Fourier transform infrared (IR) spectrophotometer (Thermo Nicolet) equipped with an Ever-Glo mid/far IR source, a potassium bromide (KBr) beamsplitter, and a mercury cadmium telluride (MCT-A) detector. The IR wavelength verification was performed using polystyrene, and the TG calibration standards were nickel and Alumel™. The sample was placed in a platinum sample pan, and the pan was inserted into the TG furnace. The TG instrument was started first, immediately followed by the FT-IR instrument. The TG instrument was operated under a flow of helium at 90 and 10 cc/min for the purge and balance, respectively. The furnace was heated under helium at a rate of 20° C./minute to a final temperature of 97° C. IR spectra were collected approximately every 16 seconds for approximately 13 minutes. Each IR spectrum represents 16 co-added scans collected at a spectral resolution of 4 $cm^{-1}$. Volatiles were identified from a search of the High Resolution Nicolet Vapor Phase spectral library (v. 1990-1994).

Hot Stage Microscopy

Hot stage microscopy was performed using a Linkam hot stage (FTIR 600) mounted on a Leica DM LP microscope equipped with a SPOT Insight™ color digital camera. Temperature calibrations were performed using USP melting point standards. Samples were placed on a cover glass, and a second cover glass was placed on top of the sample. As the stage was heated, each sample was visually observed using a 20× objective with crossed polarizers and a first order red compensator. Images were captured using SPOT software (v. 4.5.9).

Karl-Fischer Titration (KF)

Coulometric KF analysis for water determination was performed using a Mettler Toledo DL39 KF titrator. A blank titration was carried out prior to analysis. The sample was prepared under a dry nitrogen atmosphere, where 11 to 78 mg of the sample was dissolved in approximately 1 mL dry Hydranal-Coulomat AD in a pre-dried vial. The entire solution was added to the KF coulometer through a septum and mixed for 10 seconds. The sample was then titrated by means of a generator electrode, which produces iodine by electrochemical oxidation: $2\ I^- \rightarrow I_2 + 2e^-$. Two replicates were obtained to ensure reproducibility.

Fourier Transform Infrared (IR) Spectroscopy

IR spectra were acquired on Nexus 670® IR spectrophotometer (Thermo Nicolet) equipped with an Ever-Glo mid/far IR source, a potassium bromide (KBr) beamsplitter and a deuterated triglycine sulfate (DTGS) detector. Wavelength verification was performed using NIST SRM 1921b (polystyrene). An attenuated total reflectance (ATR) accessory (Thunderdome™, Thermo Spectra-Tech), with a germanium (Ge) crystal was used for data acquisition. Each spectrum represents 256 co-added scans collected at a spectral resolution of 4 $cm^{-1}$. A background data set was acquired with a clean Ge crystal. A Log 1/R (R=reflectance) spectrum was obtained by taking a ratio of these two data sets against each other.

Fourier Transform Raman (Raman) Spectroscopy

Raman spectra were acquired on a Raman module interfaced to a Nexus 670 IR spectrophotometer (Thermo Nicolet) equipped with an indium gallium arsenide (InGaAs) detector. Wavelength verification was performed using sulfur and cyclohexane. Each sample was prepared for analysis by placing the sample into a glass tube, capillary or pellet and positioning in a gold-coated holder. Approximately 1 W of Nd:YVO$_4$ laser power (1064 nm excitation wavelength) was used to irradiate the sample. The data acquisition parameters for each spectrum are displayed above the image in Appendix C Solution Proton Nuclear Magnetic Resonance ($^1$H-NMR)

The $^1$H-NMR spectra were acquired with a Varian $^{UNITY}$INOVA-400 spectrometer. The sample samples were prepared by dissolving approximately 3 to 13 mg of sample in DMSO-d$_6$ containing TMS. The data acquisition parameters are displayed in the first plot of the spectrum in Appendix C.

Solid-state Carbon Nuclear Magnetic Resonance ($^{13}$C-NMR)

The $^{13}$C-NMR solid-state NMR spectra were acquired with a Varian $^{UNITY}$INOVA-400 spectrometer. The samples were prepared by packing them into 4 mm PENCIL type zirconia rotors and rotating at 12 kHz at the magic angle. The data acquisition parameters are displayed in the first plot of the spectrum in Appendix C.

Dynamic Vapor Sorption (DVS)

DVS data were collected on a VTI SGA-100 Vapor Sorption Analyzer. NaCl and PVP were used as calibration standards. Samples were not dried prior to analysis. Sorption and desorption data were collected over a range from 5 to 95% RH (or 55 to 95% RH for Form B) at 10% RH increments under a nitrogen purge. The equilibrium criterion used for analysis was less than 0.0100% weight change in 5 minutes with a maximum equilibration time of 3 hours. Data were not corrected for the initial moisture content of the samples.

XRPD Indexing

XRPD patterns of treprostinil Forms A and B were indexed using X'Pert High Score Plus [12]. Agreement between the allowed peak positions, marked with red bars, and the observed peaks indicates a consistent unit cell determination. Space groups consistent with the assigned extinction symbol, unit cell parameters, and derived quantities are tabulated below the figures. Indexing and structure refinement are computational studies which are performed under the "Procedures for SSCI Non-cGMP Activities."

* * *

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention. All of the publications, patent applications and patents cited in this specification are incorporated herein by reference in their entirety.

What is claimed is:

1. A treprostinil Form C having an X-ray powder diffractogram comprising the following peak: 6.55 °2θ±0.2 °2 θ, as determined on a diffractometer using Cu-Kα radiation at a wavelength of 1.54059 Å, in substantially pure form.

Figure 16:
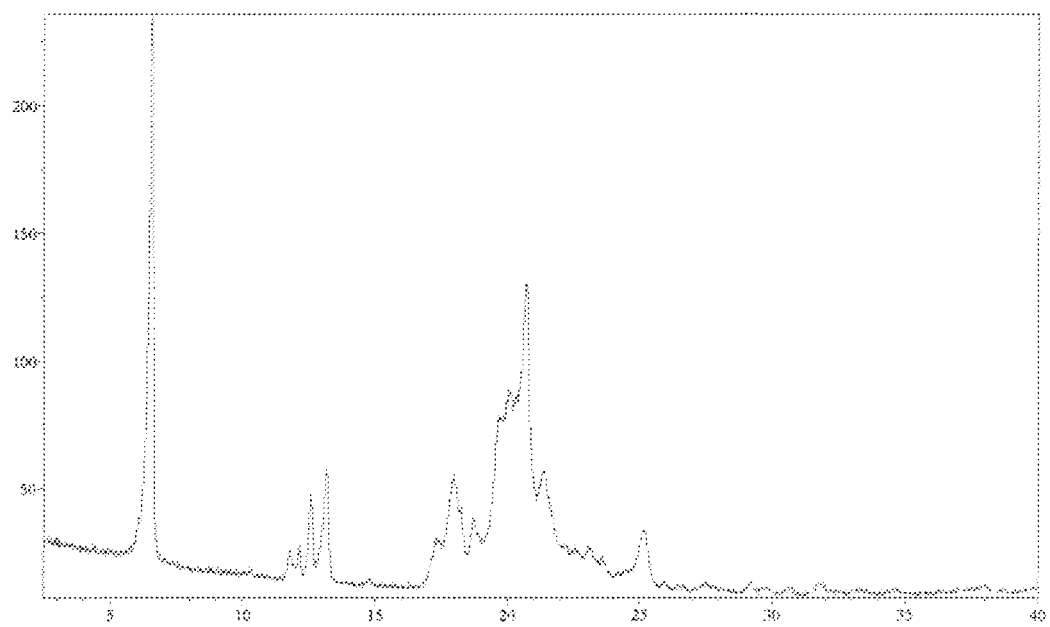
FIG. 16 is an X-ray powder diffraction pattern of treprostinil Form C.

2. The treprostinil Form C of claim 1, wherein the diffractogram is substantially as shown in FIG. 16.

3. The treprostinil Form C of claim 1 having a purity of at least 90% aside from residual solvents.

4. The treprostinil Form C of claim 3 having the purity of at least 95% aside from the residual solvents.

5. The treprostinil Form C of claim 3 having the purity of at least 98% aside from the residual solvents.

6. The treprostinil Form C of claim 3 having the purity of at least 99% aside from the residual solvents.

7. The treprostinil Form C of claim 3 having the purity of at least 99.9% aside from the residual solvents.

8. The treprostinil Form C of claim 3, wherein the purity is determined by NMR integration or by analyzing an X-ray powder diffractogram.

9. The treprostinil Form C of claim 1 that is substantially free of any other form of crystalline treprostinil.

10. The treprostinil Form C of claim 1, wherein a differential scanning calorimetry (DSC) curve of Form C comprises a minor endotherm at about 78.3° C. and a major endotherm at about 126.3° C.

11. The treprostinil Form C of claim 10, wherein the DSC curve is substantially as shown in FIG. 17.

12. The treprostinil Form C of claim 1 in an amount of 1 gram to 50 kg.

13. A method of making treprostinil Form C of claim 1, comprising exposing treprostinil monohydrate Form A or treprostinil monohydrate Form B to a reduced pressure and a temperature less than 42° C.

14. A pharmaceutical formulation comprising treprostinil Form C of claim 1 and a pharmaceutically carrier or excipient.

15. A solid dosage form for oral administration comprising treprostinil Form C of claim 1 mixed with at least one inert pharmaceutical carrier.

16. The solid dosage form of claim 15, which is a capsule, a tablet, a pill, a powder or a granule.

17. A crystalline treprostinil monohydrate Form A, having an X-ray powder diffractogram comprising the following peaks: 11.6, 16.2, and 20.0 °2θ±0.2 °2θ, as determined on a diffractometer using Cu-Kα radiation at a wavelength of 1.54059 Å, in substantially pure form.

18. The crystalline treprostinil monohydrate Form A of claim 17, wherein the diffractogram further comprises peaks at 5.2, 21.7, and 27.7 °2θ±0.2 °2θ.

Figure 2:
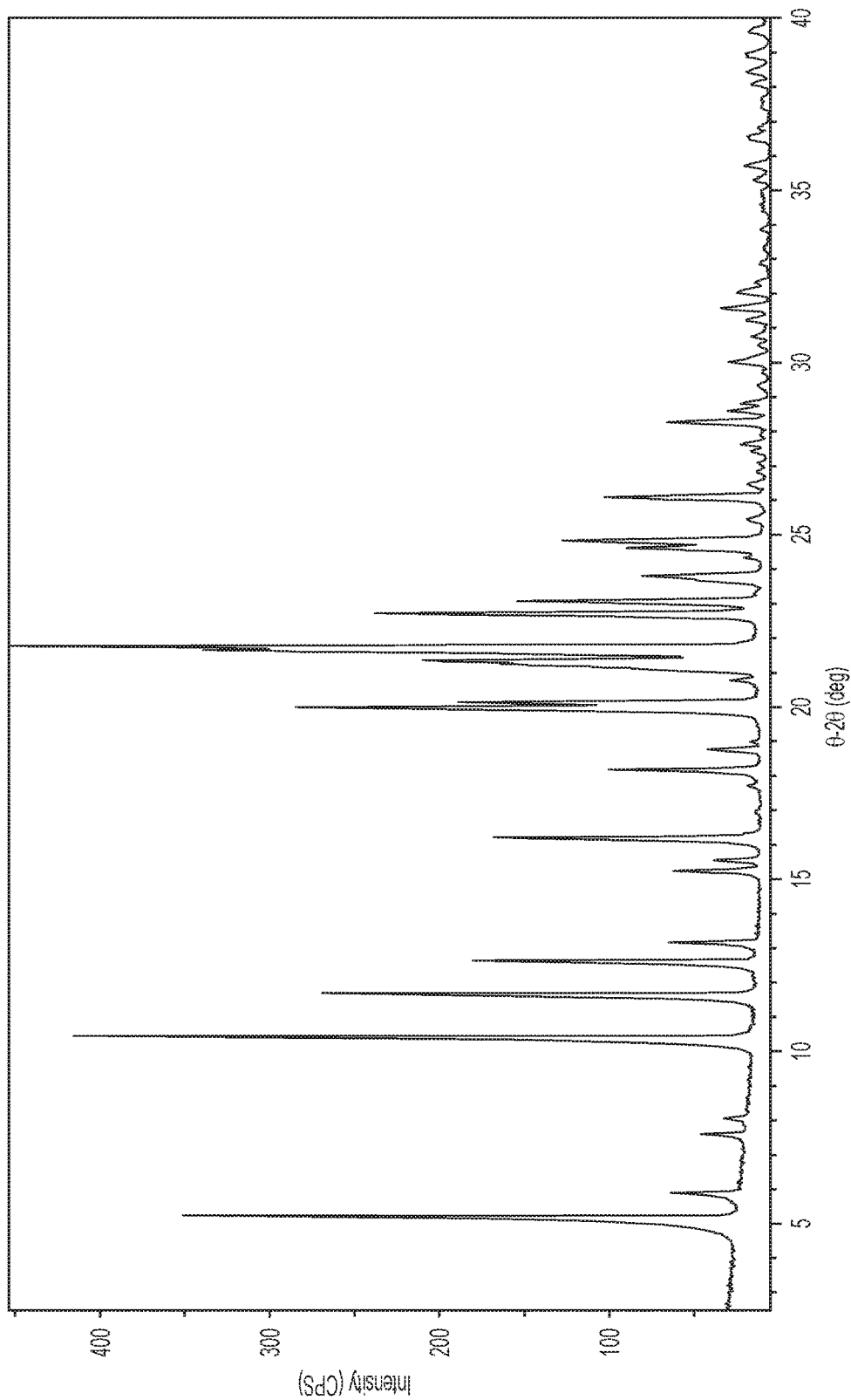
FIG. 2 is an X-ray powder diffraction pattern of treprostinil monohydrate Form A.

19. The crystalline treprostinil monohydrate Form A of claim 17, wherein the diffractogram is as shown in FIG. 2.

20. The crystalline treprostinil monohydrate Form A of claim 17, wherein the crystalline treprostinil monohydrate form A has a differential scanning calorimetry (DSC) curve that comprises a minor endotherm at about 78.3° C. and a major endotherm at about 126.3° C.

21. The crystalline treprostinil monohydrate Form A of claim 20, wherein the DSC curve is as shown in FIG. 3.

22. The crystalline treprostinil monohydrate Form A of claim 17 having a purity of at least 90% aside from residual solvents.

23. The crystalline treprostinil monohydrate Form A of claim 22 having the purity of at least 95% aside from the residual solvents.

24. The crystalline treprostinil monohydrate Form A of claim 22 having the purity of at least 98% aside from the residual solvents.

25. The crystalline treprostinil monohydrate Form A of claim 22 having the purity of at least 99% aside from the residual solvents.

26. The crystalline treprostinil monohydrate Form A of claim 22 having the purity of at least 99.9% aside from the residual solvents.

27. The crystalline treprostinil monohydrate Form A of claim 22, wherein the purity is determined by NMR integration or by analyzing an X-ray powder diffractogram.

28. The crystalline treprostinil monohydrate Form A of claim 17, wherein said Form A is free of any other form of crystalline treprostinil.

29. The crystalline treprostinil monohydrate Form A of claim 17 in an amount of 1 gram to 50 kg.

30. A crystalline treprostinil monohydrate Form B, having an X-ray powder diffractogram comprising the following peaks: 5.9, 12.1, and 24.4 °2θ±0.2 °2θ, as determined on a diffractometer using Cu-Kα radiation at a wavelength of 1.54059 Å, in substantially pure form.

31. The crystalline treprostinil monohydrate Form B of claim 30, wherein the diffractogram further comprises peaks at 10.7, 20.6, and 22.3°2θ±0.2°2θ.

Figure 9:
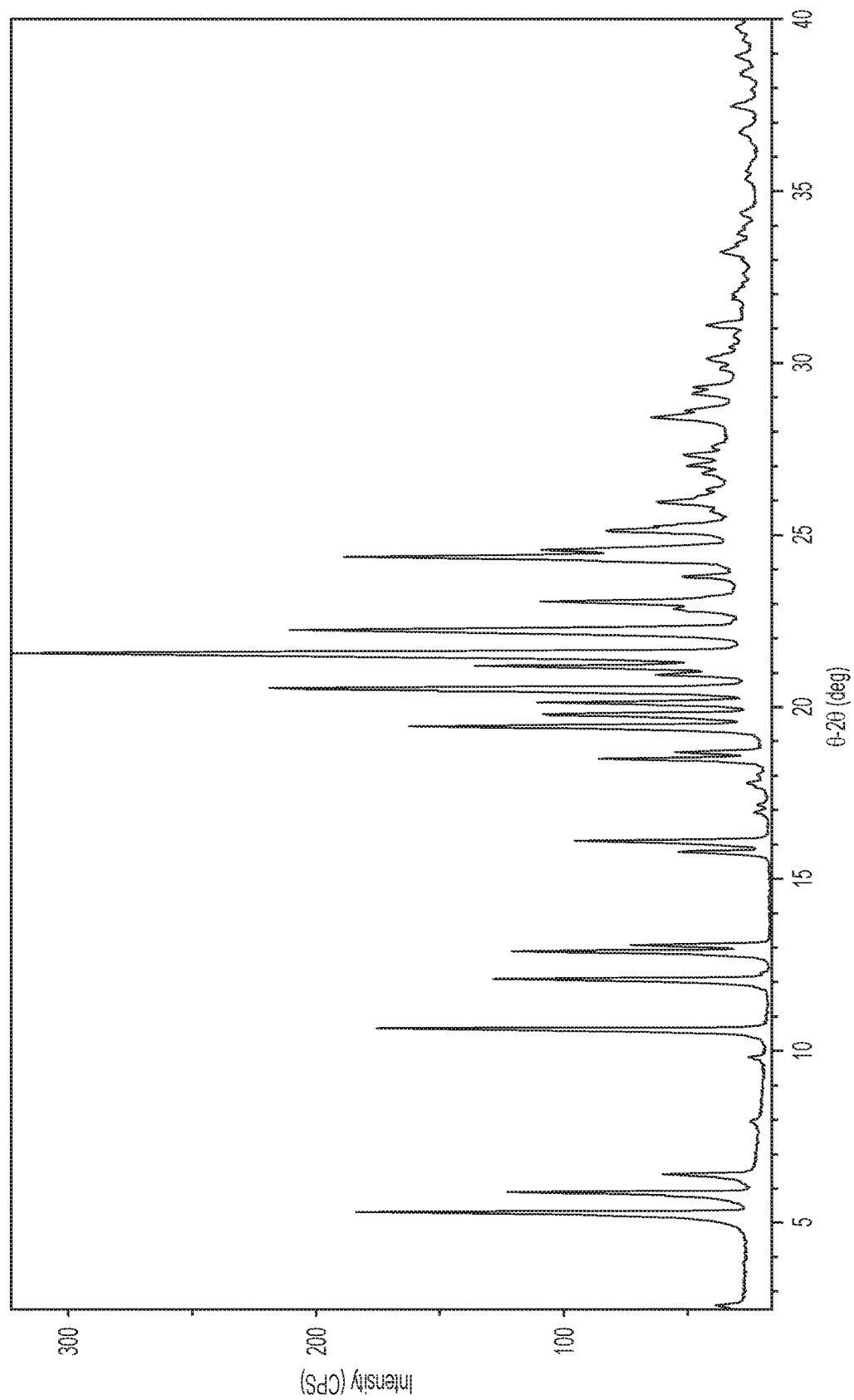
FIG. 9 is an X-ray powder diffraction pattern of treprostinil monohydrate Form B.

32. The crystalline treprostinil monohydrate Form B of claim 30, wherein the diffractogram is as shown in FIG. 9.

33. The crystalline treprostinil monohydrate Form B of claim 30, wherein the crystalline treprostinil monohydrate Form B has a differential scanning calorimetry (DSC) curve that comprises a minor endotherm at about 74.8° C. and a major endotherm at about 125.2° C.

34. The crystalline treprostinil monohydrate Form B of claim 33, wherein the DSC curve is as shown in FIG. 10.

35. The crystalline treprostinil monohydrate Form B of claim 30 having a purity of at least 90% aside from residual solvents.

36. The crystalline treprostinil monohydrate Form B of claim 35 having the purity of at least 95% aside from the residual solvents.

37. The crystalline treprostinil monohydrate Form B of claim 35 having the purity of at least 98% aside from the residual solvents.

38. The crystalline treprostinil monohydrate Form B of claim 35 having the purity of at least 99% aside from the residual solvents.

39. The crystalline treprostinil monohydrate Form B of claim 35 having the purity of at least 99.9% aside from the residual solvents.

40. The crystalline treprostinil monohydrate Form B of claim 35, wherein the purity is determined by NMR integration or by analyzing an X-ray powder diffractogram.

41. The crystalline treprostinil monohydrate Form B of claim 30, wherein said Form B is free of any other form of crystalline treprostinil.

42. The crystalline treprostinil monohydrate Form B of claim 30 in an amount of 1 gram to 50 kg.

* * * * *